(12) United States Patent
Sörnmo et al.

(10) Patent No.: US 8,311,619 B2
(45) Date of Patent: *Nov. 13, 2012

(54) DETECTION OF DRASTIC BLOOD PRESSURE CHANGES

(75) Inventors: Leif Sörnmo, Lund (SE); Kristian Solem, Lund (SE)

(73) Assignee: Gambro Lundia AB, Lund (SE)

( * ) Notice: Subject to any disclaimer, the term of this patent is extended or adjusted under 35 U.S.C. 154(b) by 425 days.

This patent is subject to a terminal disclaimer.

(21) Appl. No.: 12/066,478

(22) PCT Filed: Aug. 10, 2006

(86) PCT No.: PCT/SE2006/050280
§ 371 (c)(1),
(2), (4) Date: Aug. 27, 2008

(87) PCT Pub. No.: WO2007/032732
PCT Pub. Date: Mar. 22, 2007

(65) Prior Publication Data
US 2008/0319332 A1 Dec. 25, 2008

Related U.S. Application Data

(60) Provisional application No. 60/716,393, filed on Sep. 12, 2005.

(30) Foreign Application Priority Data

Sep. 12, 2005 (SE) .................................. 0502018

(51) Int. Cl.
*A61B 5/04* (2006.01)
*A61B 5/02* (2006.01)
(52) U.S. Cl. ................. 600/515; 600/513; 600/485
(58) Field of Classification Search .................. 600/481, 600/455, 485, 508–528
See application file for complete search history.

(56) References Cited

U.S. PATENT DOCUMENTS 4,718,891 A    1/1988  Lipps
5,090,418 A    2/1992  Squires et al.
5,615,684 A *  4/1997  Hagel et al. ................. 600/513

(Continued)

FOREIGN PATENT DOCUMENTS

EP      0 956 817 A1    11/1999
WO      WO 99/59466     11/1999

OTHER PUBLICATIONS

K. Solem, et al., "Detection of Hypotension during Hemodialysis Using the ECG," Computers in Cardiology 2004, 31 (2004), pp. 717-720.

(Continued)

*Primary Examiner* — Niketa Patel
*Assistant Examiner* — Catherine Voorhees
(74) *Attorney, Agent, or Firm* — Finnegan, Henderson, Farabow, Garrett & Dunner, LLP

(57) ABSTRACT

A cardiac-activity based prediction of a rapid drop in a patient's blood pressure during extracorporeal blood treatment is disclosed. A proposed alarm apparatus includes a primary beat morphology analysis unit bank of secondary analysis units and an alarm generating unit. The primary beat morphology analysis unit discriminates heart beats in a received basic electrocardiogram signal, classifies each beat into one out of at least two different beat categories, and associates each segment of the signal with relevant event-type data. The event-type data and the basic electrocardiogram signal together form an enhanced electrocardiogram signal, based upon which the primary beat morphology analysis unit determines whether one or more secondary signal analyses should be performed. Depending on the enhanced electrocardiogram signal's properties, the bank of secondary analysis units performs none, one or more of up to at least two different types of secondary analyses, and for each analysis performed produces a respective test signal. The alarm generating unit receives the test signals, and triggers an alarm signal indicative of an estimated rapid blood pressure decrease, if at least one alarm criterion is fulfilled.

22 Claims, 6 Drawing Sheets

U.S. PATENT DOCUMENTS

| | | | |
|---|---|---|---|
| 5,817,027 A * | 10/1998 | Arand et al. | 600/515 |
| 6,050,951 A * | 4/2000 | Friedman et al. | 600/485 |
| 6,241,682 B1 * | 6/2001 | Ochiai et al. | 600/510 |
| 7,062,314 B2 * | 6/2006 | Zhu et al. | 600/515 |
| 7,079,888 B2 * | 7/2006 | Oung et al. | 600/513 |
| 7,171,260 B2 * | 1/2007 | Lee et al. | 600/516 |
| 7,181,277 B1 * | 2/2007 | Shelchuk et al. | 607/9 |
| 7,272,435 B2 * | 9/2007 | Rowlandson | 600/513 |
| 2002/0095094 A1 | 7/2002 | Hutten et al. | |
| 2003/0009106 A1 * | 1/2003 | Sitzman et al. | 600/513 |
| 2004/0054292 A1 | 3/2004 | Sun et al. | |
| 2004/0167417 A1 | 8/2004 | Schulhauser et al. | |
| 2005/0148890 A1 * | 7/2005 | Hastings | 600/509 |
| 2006/0106323 A1 * | 5/2006 | Bischoff et al. | 600/515 |
| 2009/0082684 A1 * | 3/2009 | Sornmo et al. | 600/513 |

OTHER PUBLICATIONS

S. Severi, et al., "Heart rate variability spectral indices for haemodynamic classification of haemodialysis patients," Physiol. Meas. 18 (1997), pp. 339-353.

O. Shapira, et al., "ECG Changes and Cardiac Arrhythmias in Chronic Renal Failure Patients on Hemodialysis," Journal of Electrocardiology vol. 25, No. 4 (1992), pp. 273-279.

* cited by examiner

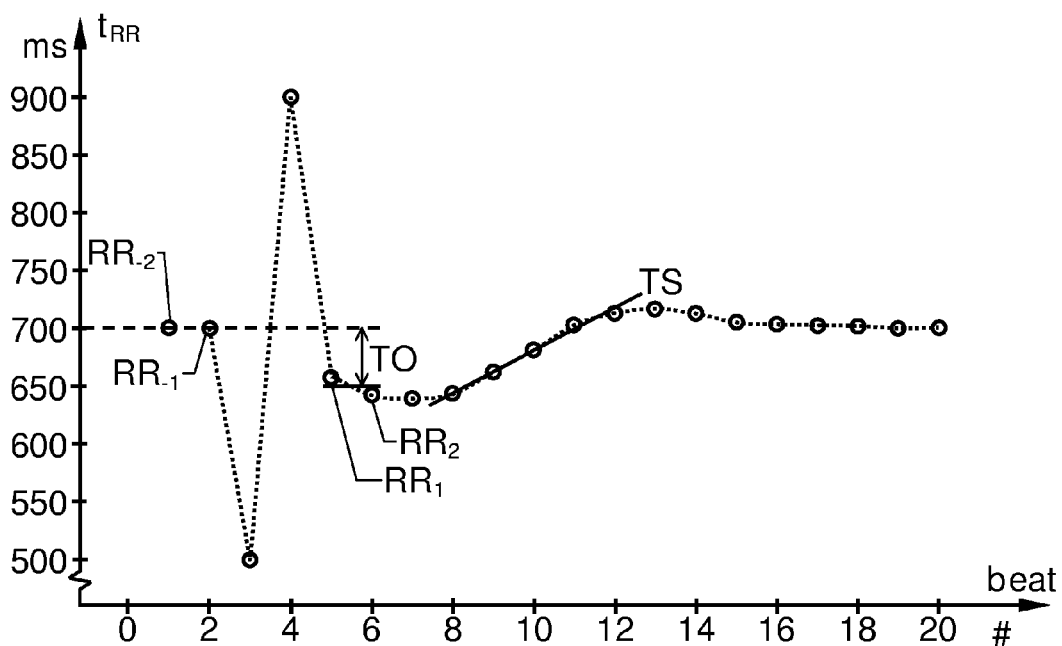
Fig. 9
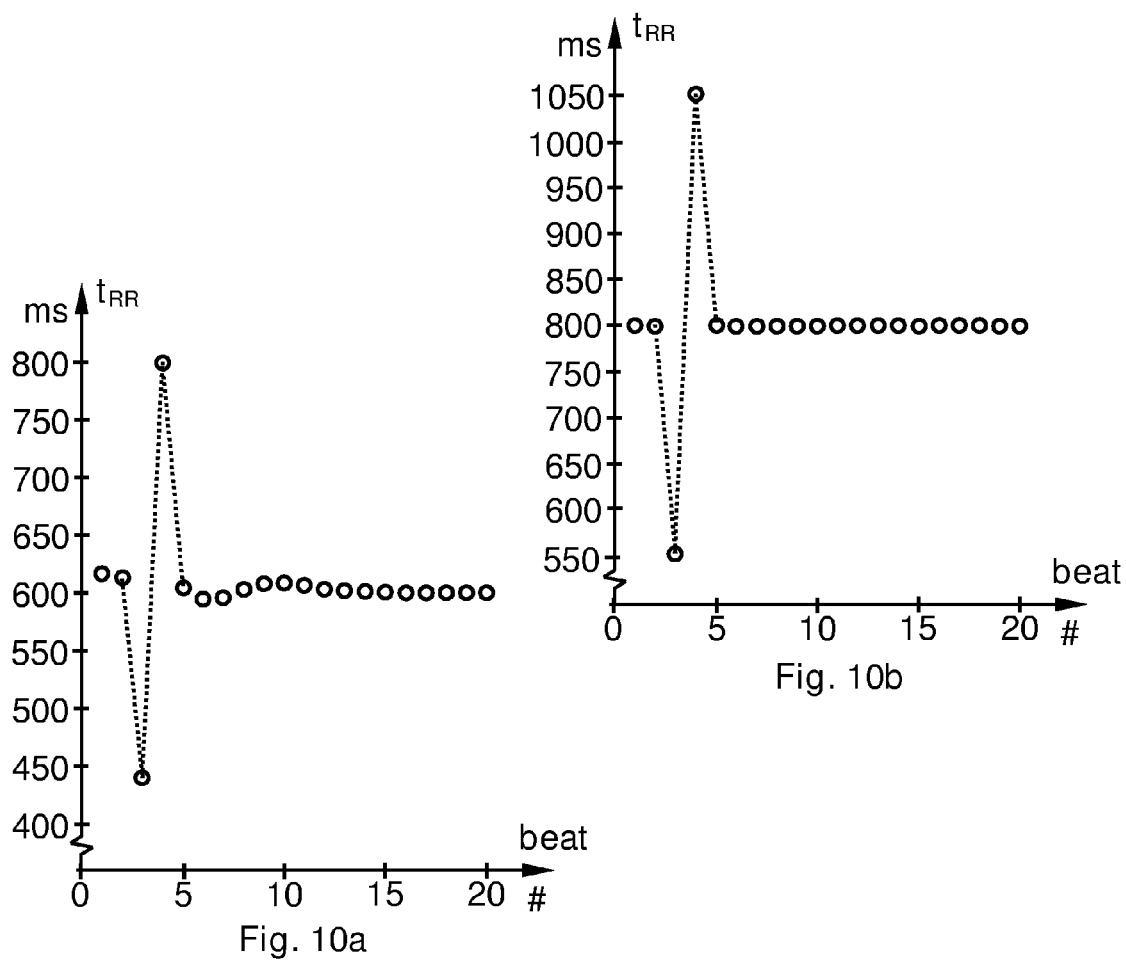
Fig. 10a
Fig. 10b

DETECTION OF DRASTIC BLOOD PRESSURE CHANGES

CROSS REFERENCE TO RELATED APPLICATIONS

This application is a national phase application based on PCT/SE2006/050280, filed Aug. 10, 2006, the content of which is incorporated herein by reference, and claims the priority of Swedish Patent Application No. 0502018-5, filed Sep. 12, 2005, and the benefit of U.S. Provisional Application No. 60/716,393, filed Sep. 12, 2005, the content of both of which is also incorporated herein by reference.

THE BACKGROUND OF THE INVENTION AND PRIOR ART

The present invention relates generally to detection of the onset of a rapid drop in a patient's blood pressure during extracorporeal blood treatments, such as hemodialysis, hemofiltration or hemodiafiltration.

The human body consists of approximately 60% water—a level which is important to maintain for survival. While it is unproblematic to provide the body with new water, disposal of surplus water is a major problem in renal patients. The task of the normal kidney is to remove superfluous fluid from the blood, such as water, urea and other waste products. The resulting urine is transferred to the bladder and finally leaves the body during urination. The kidney's second task is to regulate for example the balance of acid and base. With malfunctioning kidneys, disorders may develop in most major body organs, a syndrome called uremia. If uremia remains untreated, it will lead to death. Uremia is treated either by kidney transplantation, or some for of extracorporeal blood treatment.

During extracorporeal blood treatment it is common that the patient suffers from symptomatic hypotension (i.e. a rapid blood pressure decrease), followed by nausea, vomiting and sometimes fainting. Such an event is not only strenuous for the patient, but also requires considerable attention from the staff overseeing the treatment. Consequently, during extracorporeal blood treatment, it is highly desirable to detect the onset of symptomatic hypotension and preventing it from coming about.

In recent years, the connection between heart rate variability (HRV) and hypotension has been studied. HRV analysis has been proven to be a useful noninvasive tool for assessing information on the state of the autonomatic nervous system, and thus parasympathetic and sympathetic activity. If the HRV is analyzed in the frequency domain, the spectrum is often divided into two sub-bands: a low-frequency (LF) band, e.g. 0.04 Hz to 0.15 Hz, and a high-frequency (HF) band, e.g. 0.15 to 0.40 Hz. The effect on HRV due to changes in the autonomatic balance has been investigated in many studies, with the main conclusion that the LF band is influenced by sympathetic activity, whereas parasympathetic activity influences the HF band. Moreover, determinants of HRV in hemodialysis patients have been studied as well as autonomic dysfunction during hemodialysis.

In addition, the relationship between HRV and blood pressure during hemodialysis has been investigated. For instance, the patent document U.S. Pat. No. 4,718,891 describes an automated hemodialysis control based on this relationship. Although being silent about dialysis treatment, the published International Patent Application WO99/59466 discloses a combined electrocardiogram (ECG) and blood-pressure measuring apparatus.

Today, little is known about sequential changes in the activity of the autonomatic nervous system, which occur just before and during a hypotensive episode. So far, the major attention has been focused on the relation between the power in the LF and the HF band, the so-called LF/HF ratio, in hypotension-prone and hypotension-resistant uremic patients. It has been concluded that the LF/HF ratio can be used as a hypotension marker in patients receiving extracorporeal blood treatment, since significant increase of the LF/HF ratio is observed during extracorporeal blood treatment sessions not complicated by hypotension, whereas at the time of collapse, the LF/HF ratio fell markedly in sessions with hypotension. It has also been suggested that the LF/HF ratio may reveal differences between groups with different propensity to hypotension, and can thus give a deeper insight into the autonomatic control during extracorporeal blood treatment. Hence, the LF/HF ratio appears to be a useful index for discriminating between hypotension-prone and hypotension-resistant patients. The sympathovagal balance has also been identified as a major determinant of short-term blood pressure variability. The sympathovagal balance describes the dual, opposing effects of the sympathetic and parasympathetic nervous systems on the sinus node.

In the article, "ECG Changes and Cardiac Arrhythmias in Chronic Renal Failure Patients on Hemodialysis", Journal of Electro-cardiology, Vol. 25, No. 4, October 1992, Shapira, O. M. et al. describe that patients with chronic renal failure frequently exhibit ECG changes and a high incidence of ventricular and supra-ventricular arrhythmias, which may be prognostically significant during and after extracorporeal blood treatment. One very important effect of cardiac arrhythmias and other beat abnormalities, which may occur during extracorporeal blood treatment, is that these events disturb the above-mentioned HRV analysis. As a result, the HRV-based techniques for predicting/detecting hypotension fail when ventricular ectopic beats (VEB) and supra-ventricular ectopic beats (SVEB) are too frequent. In such cases, the premature beats disrupt the neurocardiac modulation of the sinus rhythm and render adjacent RR-intervals useless for HRV analysis.

In the article "Detection of Hypotension during Hemodialysis using the ECG", Computers in Cardiology 2004; Chicago, Ill., United States, Sep. 19-22, 2004, Solem, K., et al. describe a strategy for estimating a patient's propensity to hypotension at an early stage of hemodialysis based on evaluation of HRV and ectopic beat patterns.

However, there is yet no solution being capable of, on one hand, modeling the beat abnormality aspects of cardiac activity sufficiently well in order to detect, or predict, a rapid blood pressure change arising during an ongoing extracorporeal blood treatment; and on the other hand, minimizing the amount of unnecessary signal processing (i.e. relating to cardiac properties being irrelevant with regard to the patient's specific condition).

SUMMARY OF THE INVENTION

The object of the present invention is therefore to alleviate the problems above and thus accomplish a solution by means of which the onset of a rapid blood pressure decrease can be detected at a point in time when any effects thereof, such as nausea and fainting, still can be avoided.

According to one aspect of the invention, the object is achieved by the initially described alarm apparatus, wherein the apparatus includes a primary beat morphology analysis unit, a bank of secondary analysis units and an alarm generating unit. The primary beat morphology analysis unit is adapted to: discriminate heart beats in the basic electrocardiogram signal, classify each discriminated heart beat into one out of at least two different beat categories, and associate each signal segment of the basic electrocardiogram signal with event-type data reflecting a beat category represented by the signal during that segment. The event-type data and the basic electrocardiogram signal together form an enhanced electrocardiogram signal. The primary beat morphology analysis unit also determines a number of secondary signal analyses to be performed in respect of the basic electrocardiogram signal. The number may here be anything from zero up to at least two. The bank of secondary analysis units is adapted to receive the enhanced electrocardiogram signal, and based thereon perform up to at least two different types of secondary analyses in response to control instructions from the primary beat morphology analysis unit. The bank produce a respective test signal for each analysis performed. The alarm generating unit receives the test signals and investigates whether any of the test signals fulfill at least one alarm criterion. If this is the case, the unit triggers an alarm signal indicative of an estimated rapid blood pressure decrease.

An important advantage attained by this design is that the detrimental influence of ectopic beats may essentially be removed from the heart rate variability analysis. Thus, various alarm criteria can be tested with a high degree of certainty. Furthermore, the onset of a rapid blood pressure decrease may be detected also when the intensity of ectopic beats is high, and insufficient heart rate turbulence, another important factor related to the onset of a rapid blood pressure decrease, may also detected at an early stage. Hence, the proposed detections/estimations of the hypotension risk complement one another very well, and are capable of characterizing the most important aspects of cardiac activity.

According to a preferred embodiment of this aspect of the invention, the bank of secondary analysis units includes at least two different secondary analysis units. These units are selected from a group of a heart-rate-variability analysis unit, an ectopic-beat count unit and a heart-rate-turbulence analysis unit. The heart-rate-variability analysis unit is adapted to produce a first test signal describing a ratio between a low-frequency band and a high-frequency band of a power spectrum representation of the electrocardiogram signal. The ectopic-beat count unit is adapted to produce a second test signal describing an intensity of ectopic beats, and the heart-rate-turbulence analysis unit is adapted to produce at least one third test signal describing at least one heart-rate-turbulence parameter.

By performing a number of different analyses, the chances are further improved that the onset of a rapid blood pressure decrease is detected at an early point in time. According to a preferred embodiment of this aspect of the invention, the alarm generating unit is adapted to trigger the alarm signal: if the first test signal fulfills a first alarm criterion, if the second test signal fulfils a second alarm criterion, or if the at least one third test signal fulfils at least one third alarm criterion.

According to another preferred embodiment of this aspect of the invention, the first alarm criterion is fulfilled if the first test signal is below a first threshold value. The second alarm criterion is considered to be fulfilled if the second test signal exceeds a second threshold value. Preferably, the second threshold value represents a number equivalent to approximately four times a mean intensity of ectopic beats. Namely, by studying a mean parameter rather than an absolute ditto, a more reliable marker is attained. Moreover, a factor around four has been found to produce stable and reliable hypotension detection.

According to yet another preferred embodiment of this aspect of the invention, the at least one third test signal includes a first parameter, a second parameter and/or a pair of third quantities. The first parameter expresses a turbulence-onset measure reflecting a relative change in the RR-intervals of the electrocardiogram signal during a period following a particular ectopic beat. The second parameter expresses a turbulence-slope measure reflecting a rise rate of the RR-intervals during a period following a particular ectopic beat. The pair of third quantities expresses geometric properties of a Poincaré plot in respect of the RR-intervals of the electrocardiogram signal. These parameters allow a large freedom as how to accomplish a desired test of the heart rate turbulence. Preferably, the at least one third alarm criterion is fulfilled if: the first parameter exceeds a first turbulence threshold value, the second parameter is outside an interval delimited by a lower second turbulence value and an upper second turbulence value, and/or the pair of third quantities are estimated to represent an RR-interval variation below a third threshold value.

According to a further preferred embodiment of this aspect of the invention, the first parameter is determined as a difference between an average RR-interval shortly after a particular ectopic beat, say two RR-intervals, and an average RR-interval shortly before this ectopic beat, say two RR-intervals, divided by said average RR-interval shortly before the ectopic beat. Moreover, the first turbulence threshold value preferably represents a zero alteration of the RR-interval between shortly before to shortly after said ectopic beat. Hence, a reliable alarm criterion is defined.

According to still another preferred embodiment of this aspect of the invention, the second parameter is determined based on a steepest slope found over a first set of RR-intervals, say five, within a second set of RR-intervals, say fifteen, following immediately after said ectopic beat in a function that expresses a time difference between consecutive R waves. Furthermore, the lower second turbulence value preferably represents one millisecond per RR-interval (i.e. a deceleration of 1 ms/RR-interval). Thus, another reliable alarm criterion is defined.

According to another preferred embodiment of this aspect of the invention, the RR-interval variation is estimated to be below the third threshold value if, in the a pair of third quantities, a product between a first quantity and a second quantity falls below a threshold area estimate. Alternatively, the RR-interval variation is estimated to be below the third threshold value if at least one of the first and second quantities falls below a predetermined limit value, and/or a ratio between the first quantity and the second quantity falls outside a predetermined interval. Thus, a flexibility is provided also with respect to the third alarm criterion.

According to still another preferred embodiment of this aspect of the invention, the heart-rate-variability analysis unit includes a spectral analysis module, which is adapted to produce the first test signal by transforming a heart rate signal based on the enhanced electrocardiogram signal into a power spectrum representation of the electrocardiogram signal, and calculating the ratio between the low-frequency band and the high-frequency band of said power spectrum representation. In its capacity as a marker for blood pressure changes, this ratio is an advantageous test parameter for the heart rate variability. Namely, as mentioned initially, the LF band is influenced by the sympathetic activity, whereas the parasympathetic activity influences the HF band, and in extracorporeal blood treatment sessions with hypotension it has been found that the HF power increases and the LF spectral power decreases. Consequently, the LF-to-HF ratio drops markedly in connection with a blood pressure decrease.

Preferably, the LF band ranges from approximately 0.04 Hz to approximately 0.15 Hz, the HF band ranges from approximately 0.15 Hz to approximately 0.40 Hz, and the first threshold value is approximately equal to one. Under typical conditions, the signal energy tends to be relatively evenly distributed between these two sub-bands. In connection with a blood pressure decrease however, the signal energy will be shifted up in frequency, such that a larger proportion of the signal energy is present above 0.15 Hz. Nevertheless, if an appropriate first threshold value is selected, any other band division is equally well conceivable according to the invention.

According to yet another preferred embodiment of this aspect of the invention, the heart-rate-variability analysis unit includes a rate detector module, which is adapted to receive the enhanced electrocardiogram signal, and based thereon produce the heart rate signal. Thereby, a reliable source signal for the spectral analysis is created.

According to another preferred embodiment of this aspect of the invention, the event-type data includes a normal beat representing a beat whose morphology is typical for the patient. However, the event-type data also includes at least one of the beat categories: a ventricular ectopic beat representing a beat whose morphology differs substantially from a normal sinus beat, a supraventricular ectopic beat representing a beat whose morphology differs from a normal sinus beat with respect to a P-wave morphology, and a prolonged RR-interval representing a morphology wherein a time distance between two consecutive beats exceeds a typical time distance between two such beats for the patient by a predetermined proportion. Such a beat classification is desirable because it significantly facilitates a subsequent signal processing aiming at estimating the onset of a rapid blood pressure decrease.

In order to further improve the efficiency of the signal processing, the event-type data may also include an artifact type (representing a beat which neither fulfills the criteria for a normal nor for an ectopic beat), and a noise type (representing an undesired amount of energy contained in the electrocardiogram signal).

According to another aspect of the invention, the object is achieved by the initially described medical system, wherein the system further includes the proposed alarm apparatus, an electrocardiograph and a treatment control unit. The electrocardiograph is adapted to register an electrocardiogram signal of the patient. The alarm apparatus receives the electrocardiogram signal, and the treatment control unit is adapted to receive the proposed alarm signal from the alarm apparatus. In case of an alarm signal, the treatment control unit transmits a control signal to the treatment apparatus. The control signal, in turn, is adapted to cause an adjustment of at least one treatment parameter in the treatment apparatus (e.g. the ultra-filtration rate), such that an estimated risk that the patient enters a hypotension state is reduced. Of course, this system is desirable with respect to the patient's health and comfort, as well as with respect to staffing and other economical aspects.

According to a preferred embodiment of this aspect of the invention, the control signal is adapted to effect a complete interruption of the extracorporeal blood treatment performed by the treatment apparatus. Thereby, the hypotension risk is further reduced.

According to another aspect of the invention the object is achieved by the initially described method, wherein heart beats are discriminated in the basic electrocardiogram signal. Each discriminated heart beat is classified into one out of at least two different beat categories. Each signal segment of the basic electrocardiogram signal is associated with event-type data reflecting a beat category represented by the signal during that segment. The event-type data and the basic electrocardiogram signal together form an enhanced electrocardiogram signal. Moreover, the method includes determining a number (0 up to at least 2) of secondary signal analyses to be performed in respect of the basic electrocardiogram signal. Then, based on the enhanced electrocardiogram signal, up to at least two different types of secondary analyses are performed to produce a respective resulting test signal. It is investigated whether any of the test signals fulfill at least one alarm criterion, and if so, an alarm signal is triggered indicative of an estimated rapid blood pressure decrease.

The advantages of this method, as well as the preferred embodiments thereof, are apparent from the discussion hereinabove with reference to the proposed alarm apparatus.

According to a further aspect of the invention the object is achieved by a computer program directly loadable into the internal memory of a computer, comprising software for controlling the above proposed method when said program is run on a computer.

According to another aspect of the invention the object is achieved by a computer readable medium, having a program recorded thereon, where the program is to make a computer control the above proposed method.

Thus, by means of the invention, an essentially HRV-based analysis cannot only be prevented from failing in the presence of high ectopic beat intensity, but more important, a reliable pre-diction of a rapid blood pressure decrease can be achieved also under such conditions.

Further advantages, advantageous features and applications of the present invention will be apparent from the following description and the dependent claims.

BRIEF DESCRIPTION OF THE DRAWINGS

The present invention is now to be explained more closely by means of preferred embodiments, which are disclosed as examples, and with reference to the attached drawings.

DESCRIPTION OF PREFERRED EMBODIMENTS OF THE INVENTION

Figure 1A:
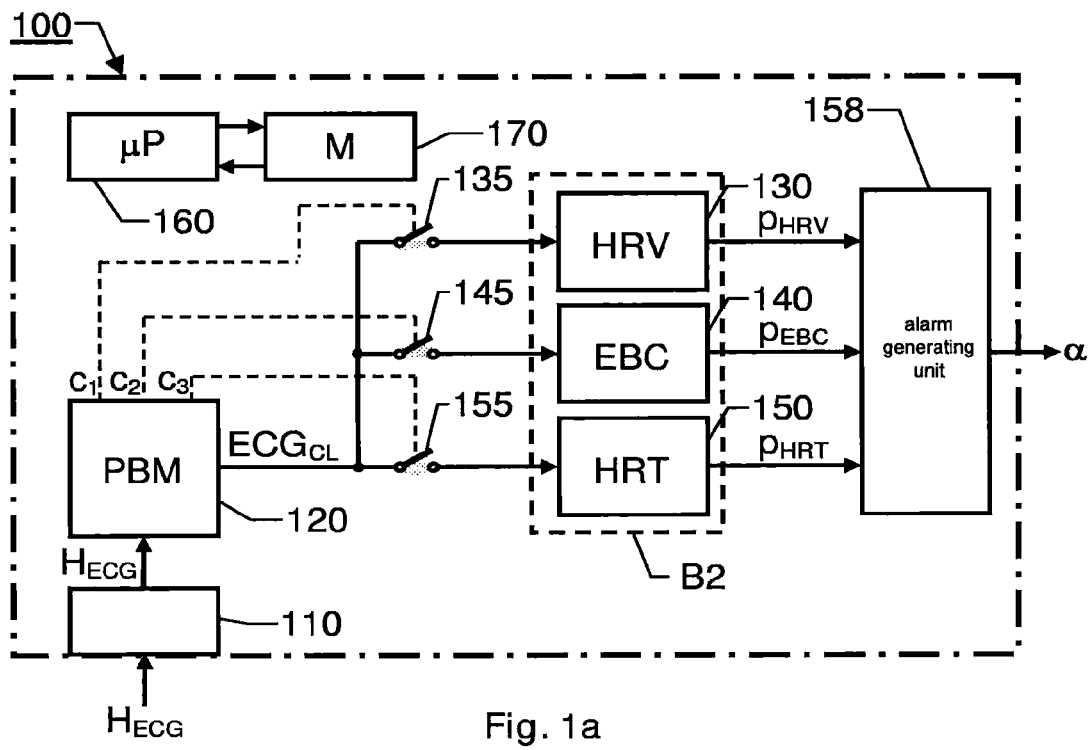
FIG. 1a shows a block diagram over an alarm apparatus according to a one embodiment of the invention.

FIG. 1 shows a block diagram over an alarm apparatus 100 for predicting a rapid blood pressure decrease in a patient undergoing extracorporeal blood treatment according to a first preferred embodiment of the invention.

The apparatus 100 includes an input interface 110, a primary beat morphology analysis unit 120, a bank of secondary analysis units B2 and an alarm-generating unit 158. Preferably, the apparatus 100 also includes a central processing unit 160 for controlling the operation of the other units, and a memory medium 170 storing a computer program which in turn is adapted to control the central processing unit 160.

The input interface 110 is adapted to receive a basic electrocardiogram signal $H_{ECG}$ of the patient. For instance, the basic electrocardiogram signal $H_{ECG}$ is a bandpass filtered, digitized signal which has been sampled at a rate of 1000 Hz and has an amplitude resolution of 0.6 μV. The electrocardiogram signal $H_{ECG}$ is preferably registered by means of a reduced set of electrodes, e.g. an EASI lead system. However, naturally, utilization of other lead systems, e.g. the standard 12-lead system is likewise conceivable according to the invention.

The primary beat morphology analysis unit 120 is adapted to discriminate heartbeats in the basic electrocardiogram signal $H_{ECG}$, and classify each discriminated beat into one out of at least two different beat categories, e.g. normal beats, ventricular ectopic beats (VEB:s), supraventricular ectopic beats (SVEB:s) and beats associated with prolonged RR-intervals. The primary beat morphology analysis unit 120 then associates each signal segment of the basic electrocardiogram signal $H_{ECG}$ with event-type data reflecting a beat category represented by the signal during that segment. This event-type data and the basic electrocardiogram signal $H_{ECG}$ together form an enhanced electrocardiogram signal $ECG_{CL}$ delivered from the unit 120.

Moreover, the primary beat morphology analysis unit 120 is adapted to determine a number of secondary signal analyses to be performed in respect of the basic electrocardiogram signal $H_{ECG}$. The number of secondary signal analyses may here be anything from zero (if no further analysis is deemed necessary) up to at least two, depending upon the characteristics of the electrocardiogram signal $H_{ECG}$. Preferably, the unit 120 generates control instructions, or signals, $c_1$, $c_2$ and $c_3$ respectively that accomplish forwarding of the enhanced electrocardiogram signal $ECG_{CL}$ to relevant secondary analysis units, for instance by activating a set of switches 135, 145 and 155.

The bank of secondary analysis units B2 is adapted to receive the enhanced electrocardiogram signal $ECG_{CL}$, and based thereon perform up to at least two different types of secondary analyses in response to the control instructions $c_1$, $c_2$ and $c_3$ from the primary beat morphology analysis unit 120. For each analysis performed, the bank of secondary analysis units B2 produces a respective test signal $p_{HRV}$, $p_{EBC}$ and $p_{HRT}$.

According to one advantageous embodiment of the invention, the bank of secondary analysis units B2 includes two or more secondary analysis units 130, 140 and/or 150. For example, a heart-rate-variability analysis unit 130 may be included, which is adapted to produce a first test signal $p_{HRV}$ describing a ratio between a low-frequency band and a high-frequency band of a power spectrum representation of the electrocardiogram signal $H_{ECG}$. The bank B2 may also include an ectopic-beat count unit 140 adapted to produce a second test signal $p_{EBC}$ describing an intensity of ectopic beats. A heart-rate-turbulence analysis unit 150, possibly included in the bank B2, is adapted to produce at least one third test signal $p_{HRT}$ that describes at least one heart-rate-turbulence parameter.

The alarm generating unit 158 is adapted to receive the test signals $p_{HRV}$, $p_{EBC}$, and/or $p_{HRT}$ from the bank of secondary analysis units B2, and investigate whether any of these signals fulfill at least one alarm criterion. If the alarm generating unit 158 finds that at least one alarm criterion is fulfilled, the unit 158 triggers an alarm signal α indicative of an estimated rapid blood pressure decrease. Preferably, the alarm generating unit 158 is adapted to trigger the alarm signal α: if the first test signal $p_{HRV}$ fulfills a first alarm criterion, if the second test signal $p_{EBC}$ fulfils a second alarm criterion, or if the at least one third test signal $p_{HRT}$ fulfils at least one third alarm criterion.

Figure 1B:
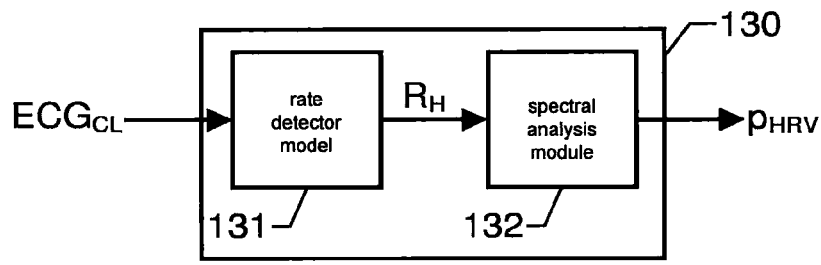
FIG. 1b shows a block diagram over a HRV analysis unit according to one embodiment of the invention.

The HRV analysis unit 130 is adapted to produce a first test signal $p_{HRV}$ based on the basic electrocardiogram signal $H_{ECG}$. FIG. 1b shows a block diagram over the HRV analysis unit 130 according to one preferred embodiment of the invention. In order to generate the first test signal $p_{HRV}$, the unit 130 preferably contains a rate detector module 131 and a spectral analysis module 132. The rate detector module 131 either receives the electrocardiogram signal $H_{ECG}$ per se, or receives an enhanced version thereof $ECG_{CL}$ produced by a beat morphology analysis unit 120, which may be included in the alarm apparatus 100 according to one preferred embodiment of the invention. The rate detector module 131 produces a heart rate signal $R_H$ based on the electrocardiogram signal $H_{ECG}$ (or the enhanced electrocardiogram signal $ECG_{CL}$). The spectral analysis module 132 then receives heart rate signal $R_H$ and transforms it into a power spectrum representation of the electrocardiogram signal $H_{ECG}$ (i.e. a signal in the frequency domain). Based on the power spectrum, the module 132 calculates a ratio between a low-frequency (LF) band and a high-frequency (HF) band of the power spectrum. According to a preferred embodiment of the invention, the LF band ranges from approximately 0.04 Hertz to approximately 0.15 Hertz, and the HF band ranges from approximately 0.15 Hertz to approximately 0.40 Hertz. The operation of the primary analysis unit will be described in further detail below.

The ectopic-beat count unit 140 is adapted to, based on the enhanced electrocardiogram signal $ECG_{CL}$, produce the second test signal $p_{EBC}$, which describes an intensity of ectopic beats. Essentially, the intensity of ectopic beats is determined by applying signal processing which counts all cardiac beats that are outside the normal sinus rhythm. Also the operation principle of the ectopic-beat count unit 140 as well as the heart-rate-turbulence analysis unit 150 will be described in further detail below. Nevertheless, according to the invention, the primary beat morphology analysis unit 120 activates a number of the analysis units 130, 140 and 150 in the bank B2 depending on certain primary analysis criteria. This activation is made based on the intensity of the ectopic beats relative to three threshold levels A, B and C associated with the HRV-, EBC- and HRT-analyses respectively. Thus, the level A is relevant to the HRV-analysis and the counting of all ectopic beats; the level B is relevant to the EBC-analysis and the counting of VEB:s and the number of prolonged intervals; and the level C is relevant to the HRT-analysis and the counting of VEB:s. The levels A, B and C may have overlap and have any interrelationships. Moreover, any combination of analyses is possible, i.e. (i) no analysis, (ii) only EBC-analysis, (iii) only HRT-analysis, (iv) only HRV-analysis, (v) a combination of EBC- and HRT-analysis, (vi) a combination of EBC- and HRV-analysis, (vii) a combination of HRT- and HRV-analysis, and (viii) a combination of all three analysis EBC, HRT and HRV.

Hence, in other words, an HRV analysis is performed if the intensity of ectopic beats is relatively low, while an EBC-analysis and/or an HRT-analysis is performed if the intensity of ectopic beats is relatively high.

The beat classification performed by the primary beat morphology analysis unit 120 preferably classify beats that represent a morphology being typical for the patient, i.e. representing the dominant normal sinus rhythm, as normal beats.

An ectopic beat (VEB, SVEB or prolonged interval), however, represents a beat whose morphology is non-typical for the patient. Preferably, the primary beat morphology analysis unit 120 is also capable of identifying artifacts and noise, and allocating relevant event-type data. This means that beats which neither fulfill the criteria for a normal nor an ectopic beat are represented as artifacts, and the remaining undesired energy of the electrocardiogram signal $H_{ECG}$ is represented as noise. Particularly, the primary beat morphology analysis unit 120 may be adapted to perform baseline filtering, QRS detection, beat characterization and beat classification of the incoming electrocardiogram signal $H_{ECG}$. According to one embodiment of the invention, the baseline filter is implemented as a linear-phase, finite impulse response lowpass filter which estimates a baseline wander followed by subtraction of this estimate from the original electrocardiogram signal $H_{ECG}$. Moreover, the baseline filter preferably complies with the American Heart Association (AHA) recommendations in terms of cutoff frequency for baseline filtering. After the baseline filtering, QRS detection is performed. Here, the beat occurrence times (i.e. the times of the R-waves) are detected. The fiducial point of each QRS complex is preferably defined by the peak location in an envelope signal obtained by summing the envelopes of each individual lead.

Following the QRS detection, each beat is classified as a normal or an ectopic beat (or an artifact or noise) based on a cross correlation method which i.e. makes use of the QRS morphology, beat-correlation and beat-SNR (signal-to-noise ratio). The cross-correlation method is initiated by using the first beat as a template beat. Each beat is subjected to linear-phase, bandpass filtering in order to remove frequencies which are deemed to be less essential for the classification. According to one preferred embodiment of the invention, the bandpass filter's cutoff frequencies are 1 and 35 Hz respectively.

Subsequently, each beat is compared to the set of template beats by computing the corresponding cross-correlation coefficients. Here, a coefficient is computed by shifting each beat in time until the best correlation is found. A new template beat is created whenever the cross-correlation drops below a noise dependent threshold value. This type of threshold design is advantageous, since it ensures that the creation of new beat classes remains within reasonable limits in noisy signals. Preferably, the noise level is measured as a root-mean-square value of the highpass filtered samples contained in the RR-interval prior to a current QRS complex. According to a preferred embodiment of the invention, this highpass filtering is performed with a cutoff frequency at 20 Hz in order to avoid that P and T waves increase the noise level. A beat classified as being similar to an existing class is used to update the template beat by means of recursive averaging, thus gradually improving the quality of the template beats.

Consequently, the unit 120 generates an output signal in the form of an enhanced electrocardiogram signal $ECG_{CL}$, which is equivalent to the electrocardiogram signal $H_{ECG}$, however where each signal segment is at least associated with relevant event-type data.

The alarm-generating unit 158 investigates whether the first test signal $p_{HRV}$ fulfills the first alarm criterion. Given that the above-mentioned LF and HF sub-bands are selected, the first alarm criterion is preferably considered to be fulfilled if the ratio is below a first threshold value, approximately equal to one.

The alarm-generating unit 158 also investigates whether the second test signal $p_{EBC}$ fulfills a second alarm criterion. Specifically, the unit 158 checks whether the second test signal $p_{EBC}$ indicates a relatively low or relatively high intensity of ectopic beats. In case of a relatively high intensity, the unit 158 triggers an alarm signal α indicative of an estimated rapid blood pressure decrease. According to one preferred embodiment of the invention, the second alarm criterion is fulfilled if the second test signal $p_{EBC}$ exceeds a second threshold value, which represents a number equivalent to approximately four times a mean intensity of ectopic beats.

Returning now to the HRV analysis performed by the unit 130. Here, the heart rate variability is determined based on the so-called heart timing (HT) representation, for instance by means of the integral pulse frequency modulation (IPFM) model. Said model may be used to simulate the variability of a series of occurrence times for normal sinus beats, and reflect the electrophysiological properties of the artria. The input signal to the IPFM model consists of the sum of a DC-level, related to the average heart rate, and a modulating signal m(t), related to the variability due to parasympathetic and sympathetic activity. The input signal to the IPFM model is integrated until a threshold, $T_0$ (representing the mean interval length between successive events) is reached. Then, an event is created at time $t_k$ as output of the model, and the integrator is reset to zero. As a result, the output signal of the IPFM model becomes an event series, which represents the heart cycle occurrences in time. In mathematical terms, the following equation defines the series of event times:

$$\int_0^{t_k} (1 + m(\tau)) d\tau = k\overline{T}_0 \tag{1}$$
$$k = 0, \ldots, N$$

where k is an integer that indexes the k:th beat following the initial beat, and the initial beat occurring at $t_0=0$. The function in (1) can be generalized to a continuous-time function by introducing the following definition:

$$\int_0^t (1 + m(\tau))\,d\tau = \kappa(t)\overline{T}_0 \qquad (2)$$

The integral can now be calculated up to any time t and is proportional to an index function κ(t) whose value at $t_k$ is identical to the integer beat index k, that is $\kappa(t_k)=k$.

The heart timing signal $d_{HT}(t)$ is defined at the event time $t_k$ as the difference between the event time $t_k$ and the expected occurrence time at the mean heart rate, $k\overline{T}_0$. The heart timing signal $d_{HT}(t)$ is closely related to the IPFM model and its modulating signal m(t). On the basis of the heart timing signal $d_{HT}(t)$, the modulating signal m(t) and especially its Fourier transform can be determined in order to produce an estimate of the HRV power spectrum.

The relationship between the heart timing signal $d_{HT}(t)$ and the modulating signal m(t) can be seen by studying the model equation (1) for a particular time $t_k$. The equation can be rewritten into:

$$\int_0^{t_k} m(\tau)\,d\tau = k\overline{T}_0 - t_k \equiv d_{HT}(t_k) \qquad (3)$$

The mean RR-interval length $\overline{T}_0$ must be estimated from the available data in order to compute $d_{HT}(t_k)$. This can be done by simply dividing the time $t_K$ of the last event with the number of events K, i.e.:

$$\overline{T}_0 = \frac{t_K}{K} \qquad (4)$$

Using the generalized IPFM model in (2), the heart timing signal $d_{HT}(t)$ can be expressed in continuous-time as:

$$d_{HT}(t) = \int_{-\infty}^{t} m(\tau)\,d\tau \qquad (5)$$

Since the modulating signal m(t) is assumed to be a causal function the integration interval can be extended to −∞. If the Fourier transform of the modulating signal m(t) and the heart timing signal $d_{HT}(t)$ are denoted $D_m(\Omega)$ and $D_{HT}(\Omega)$ respectively, we have from (5) that:

$$D_{HT}(\Omega) = \int_{-\infty}^{\infty} d_{HT}(t) e^{-j\Omega t}\,dt = \frac{D_m(\Omega)}{j\Omega} \qquad (6)$$

where $\Omega=2\pi F$ and $D_m(0)=0$ since m(t) was assumed to have a DC component equal to zero. Once the Fourier transform $D_{HT}(\Omega)$ of the heart timing signal $d_{HT}(t)$ is known a spectral estimate of the Fourier transform $D_m(\Omega)$ of the modulating signal m(t) can be computed. According to preferred embodiments of the invention, the spectral estimate $D_m(\Omega)$ is either obtained by a technique for unevenly sampled signals, or by interpolation and resampling followed use of the discrete Fourier transform (DFT).

As mentioned initially, ectopic beats introduce errors in the HRV analysis. Similar errors can also be introduced by missed beats (so-called prolonged intervals) or falsely detected beats, which may be the result of poor QRS detection. The errors are due to impulse-like artifacts in the RR-intervals introduced by the RR-intervals adjacent to an ectopic beat. The impulse will introduce a noise component in the spectral analysis. This is why the RR-intervals adjacent to an ectopic beat should not be used in the HRV analysis. The fact that ectopic beats occur in both patients and normal subjects shows that the importance of dealing with ectopic beats prior to spectra analyses of the heart rate signal.

In order to correct for an ectopic beat it is important to know whether a particular beat has a normal or ectopic origin. According to one preferred embodiment of the invention, the labeling is done with classification criteria mainly based on QRS morphology according to the above-mentioned cross-correlation method, however also based on an interval criterion. Based on QRS morphology it is relatively straightforward to discriminate ventricular ectopic beats (VEB), since their morphologies differ substantially from a normal sinus beat. The same observation holds for false events caused by artifacts. Unfortunately, however, it is not especially easy to sort out supraventricular ectopic beats (SVEB), or similar ectopic beats, since these tend to have essentially the same morphologies as normal sinus beats. The SVEB:s usually differ only with respect to P wave morphology. Nevertheless, due to noise it is impossible to make a classification exclusively based on the P wave. Thus, in order to discriminate the SVEB:s one has to use the interval-based criterion, which is much less reliable.

In general, the majority of SVEB:s are therefore classified as ectopic beats based on an RR-criterion. The same holds for the prolonged RR-intervals in connection with missing beats. An RR-interval which is prolonged (often twice the length of the mean RR-interval length) is classified as a prolonged interval (or a missing beat). A missed beat introduces impulse-like artifacts in the RR-intervals similar to those of ectopic beats. Thus, prolonged RR-intervals must also be dealt with in the HRV analysis. Moreover, a prolonged RR-interval debilitates the heart's pumping capacity in a similar way as the complete compensatory pause following a VEB.

Since ectopic beats interrupt the normal sinus modulated heart rhythm, only electrocardiogram signal $H_{ECG}$ segments containing occasional ectopic beats should be processed. In signal segments containing frequent ectopic beats the underlying sinus rhythm is too distorted to make any reliable conclusions. Therefore, according to the invention, such segments are excluded from the HRV analysis.

In the below description, we assume that sinus beats occur at times $t_0, t_1, \ldots, t_K$, and that one ectopic beat occurs at time $t_e$ in the electrocardiogram signal $H_{ECG}$ (or $ECG_{CL}$). The time $t_e$ is not included in the series $t_0, t_1, \ldots, t_K$, and the sinus beat immediately preceding the ectopic beat occurs at $t_{ke}$ and the sinus beat immediately following the occurs at $t_{ke+1}$.

According to one preferred embodiment of the invention, the ectopic beats are dealt with by first concluding that an ectopic beat modifies the occurrence times of subsequent normal beats. By estimating this time shift, δ, the presence of ectopic beats can be accounted for by the following equation:

$$d_{HT}(t_k) = \begin{cases} k\overline{T}_0 - t_k & k = 0, \ldots, k_e \\ k\overline{T}_0 - t_k + \delta & k = k_e + 1, \ldots, K \end{cases} \qquad (7)$$

In order to estimate the time shift δ we make use of (1), such that:

$$k_e \overline{T}_0 = \int_0^{t_{ke}} (1 + m(\tau)) d\tau \qquad (8)$$

and $$(k_e + 1)\overline{T}_0 = \int_{t_{ke}}^{t_{ke+1} - \delta} (1 + m(\tau)) d\tau \qquad (9)$$

Subtracting (8) from (9) gives us the equation:

$$\overline{T}_0 = \int_{t_{ke}}^{t_{ke+1}-\delta} (1 + m(\tau)) d\tau = t_{ke+1} - t_{ke} - \delta + \int_{t_{ke}}^{t_{ke+1}-\delta} m(\tau) d\tau \qquad (10)$$

We now introduce a new parameter, $\overline{m}_k$, according to:

$$\overline{m}_k = \begin{cases} \int_{t_k}^{t_{k+1}} m(\tau) d\tau & k \neq k_e \\ \int_{t_{ke}}^{t_{ke+1}-\delta} m(\tau) d\tau & k = k_e \end{cases} \qquad (11)$$

where $\overline{m}_k$ ($k \neq k_e$) is the integral of m(t) between the two normal heart beats at $t_k$ and $t_{k+1}$. This gives us:

$$\delta = t_{ke+1} - t_{ke} - \overline{T}_0 + \overline{m}_{ke} \qquad (12)$$

For the special case of a constant heart rate (a linear presumption on κ(t) or, in other words, m(t)=0 and $\overline{m}_{ke}$=0) we obtain an estimate $\hat{\delta}_0$ of the time shift δ according to:

$$\hat{\delta}_0 = t_{ke+1} - t_{ke} - \overline{T}_0 \qquad (13)$$

which is referred to as the zero order estimate of δ.

Further, we assume that the variations of the modulating signal m(t) are small within the integral interval, and thus the beat-to-beat variations in $\overline{m}_k$ are also small. Hence, a better estimate of $\overline{m}_{ke}$ is the value corresponding to the previous beat according to:

$$\hat{\overline{m}}_{ke,1} = \overline{m}_{ke-1} \qquad (14)$$

$$= \int_{t_{ke-1}}^{t_{ke}} m(\tau) d\tau$$

$$= d_{HT}(t_{ke}) - d_{HT}(t_{ke-1})$$

$$= t_{ke-1} - t_{ke} + \overline{T}_0$$

This estimate, in combination with (12), gives us a first order estimate $\hat{\delta}_1$ of the time shift δ according to:

$$\hat{\delta}_1 = t_{ke+1} - 2t_{ke} + t_{ke-1} \qquad (15)$$

Note the similarity between (13) and (15), since (15) can be rewritten as:

$$\hat{\delta}_1 = t_{ke+1} - t_{ke} - (t_{ke} - t_{ke-1}) = \hat{\delta}_0 - \hat{d}_{ke-1,0} \qquad (16)$$

where $\hat{d}_{ke-1,0}$ is the zero order estimate of $d_{ke-1}$, with $d_k$ defined as:

$$d_k = t_{k+1} - t_k + \overline{T}_0 + \overline{m}_k = 0 \quad k \neq k_e \qquad (17)$$

Note the close relationship between (12) and (17), since (17) becomes (12) when $k = k_e$.

One generalization of a higher order estimate of $\overline{m}_{ke}$ is to include variations in $\overline{m}_k$. If we continue to update the estimate of $\overline{m}_k$ according to:

$$\hat{\overline{m}}_{k,p} = \hat{\overline{m}}_{k,p-1} + \Delta \overline{m}_{k-1,p} \qquad (18)$$

where $\Delta \overline{m}_{k-1,p}$ is the p:th order difference of $\overline{m}_{k-1}$ according to:

$$\Delta \overline{m}_{k-1,p} = \Delta \overline{m}_{k-1,p-1} - \Delta \overline{m}_{k-2,p-1} \qquad (19)$$

Then it can be proven that the N:th order estimate $\hat{\delta}_N$ of the time shift δ is given by the following recursion equation:

$$\hat{\delta}_N = \hat{\delta}_{N-1} - \hat{d}_{ke-1,N-1} \quad N=1,2, \qquad (20)$$

where $$\hat{\delta}_0 = t_{ke+1} - t_{ke} - \overline{T}_0 \qquad (21)$$

Instead of using the recursion in (20), we can express the N:th order estimate $\hat{\delta}_N$ of the time shift δ directly in terms of the occurrence times:

$$\hat{\delta}_N = \sum_{l=0}^{N+1} (-1)^l \binom{N+1}{l} t_{ke+1-l} \qquad (22)$$

$$N = 1, 2, \ldots$$

and N=0 is given by (21), however cannot be used, since it makes use of the mean RR-interval length $\overline{T}_0$, which is yet unknown. Once an estimate of the time shift δ according to (22) is obtained, it is straightforward to update the estimate $\hat{\overline{T}}_0$ of the mean RR-interval length $\overline{T}_0$ according to:

$$\hat{\overline{T}}_0 = \frac{t_K - \hat{\delta}_N}{K}. \qquad (23)$$

Now $d_{HT}(t_k)$ in (7) can be calculated, since all the involved parameters are available.

Returning to the ectopic-beat count unit 140, this unit is adapted to perform an EBC analysis, where an intensity of ectopic beats is determined, i.e. the second test signal $p_{EBC}$. The occurrence times $t_k$ of the ectopic beats may be described by a point process $p_e(t)$ according to:

$$p_e(t) = \sum_{k=1}^{N} \delta(t - t_k) \qquad (24)$$

where N is the number of ectopic beats present. The ectopic-beat count unit 140 studies the changes in the behavior of the occurrence times $t_k$ of the ectopic beats. A point process is characterized by its intensity. Thus, a change in the behavior of the occurrence times $t_k$ influences the intensity in the point process. Consequently, the EBC analysis follows the changes in the intensity of a point process.

A point process only gives present information about the ectopic beats and take no count of their history, i.e. the amount of ectopic beats. In order to include this information a count process, $N_e(t)$, is used according to one preferred embodiment of the invention. The count process describes the number of ectopic beats present up until the time t, i.e. the integral of the point process $p_e(t)$, defined as:

$$N_e(t) = k \quad t_k \leq t < t_{k+1} \quad k = 0, 1, \ldots, N \qquad (25)$$

Thus, the intensity of the point process $p_e(t)$ is connected to the slope of the count process.

The beats used in the EBC analysis are those classified as VEB:s and prolonged intervals by the primary beat morphology analysis unit 120, since VEB:s and prolonged intervals have similar effects on the heart.

The EBC analysis follows the changes in the intensity of ectopic beats throughout the entire signal. According to the invention, the EBC analysis can be performed both in real time and offline. However, in order to have the alarm signal α control a treatment apparatus, the EBC analysis must be executed in real time. An instantaneous intensity of the ectopic beats in the electrocardiogram signal $H_{ECG}$ cannot be obtained. Nevertheless, the mean intensity over a time block can be computed. This analysis is preferably performed in a sliding window over the enhanced electrocardiogram signal $ECG_{CL}$. Thus, the EBC analysis follows changes in the intensity of ectopic beats blockwise. According to the invention, the intensity of ectopic beats can be measured in many ways, two of which will be explicitly described below. A first method is based on a point process representation and a second method is based on a count process.

One assumption is that the occurrence times of the ectopic beats follow a Poisson process, since the Poisson process is a point process. Thus, the distances between the occurrence times are independent and exponential distributed with the intensity λ. If the same intensity λ is assumed within a block, then the maximum likelihood estimate, $\hat{\lambda}$, of the intensity λ is according to:

$$\hat{\lambda} = \frac{K}{\sum_{k=1}^{K} x[k]} \quad (26)$$

where x[k] is the different distances between each occurrence time and K is the number of distances (i.e. one less than the number of ectopic beats). The result is intuitive, since the easiest way to measure the intensity of ectopic beats within a block is simply to count the number of ectopic beats within that block, which is basically the same as (26), since the denominator is essentially constant for large block sizes.

Alternatively, the occurrences of the ectopic beats may be described by means of the count process $N_e(t)$, and its corresponding discrete-time signal model $N_e[n]$. The count process $N_e(t)$ is a non decreasing function and may, within a block, be approximated with a straight line model according to:

$$N_e[n]=A+Bn \quad (27)$$

where B is the slope of the count process and thus an estimate of the intensity of ectopic beats.

The available data set includes the occurrence times of the ectopic beats, $\{t_k\}$ for k=1, ..., N. A data set $x^u[k]$ describing the number of ectopic beats at time $t_k$ (in accordance to a count process), can be attained from $\{t_k\}$, where $x^u[k]$ is an unevenly sampled signal. A new data set x[k] is obtained when $x^u[k]$ is interpolated and then evenly resampled. When assuming a linear model the least square error estimate $\hat{B}$ of the intensity B, for a given set of evenly sampled data, is:

$$\hat{B} = -\frac{6}{N(N+1)}\sum_{k=0}^{N-1} x[k] + \frac{12}{N(N^2-1)}\sum_{k=0}^{N-1} kx[k] \quad (28)$$

where x[k] is the distances between each occurrence time and N is the number of ectopic beats.

Figure 2:
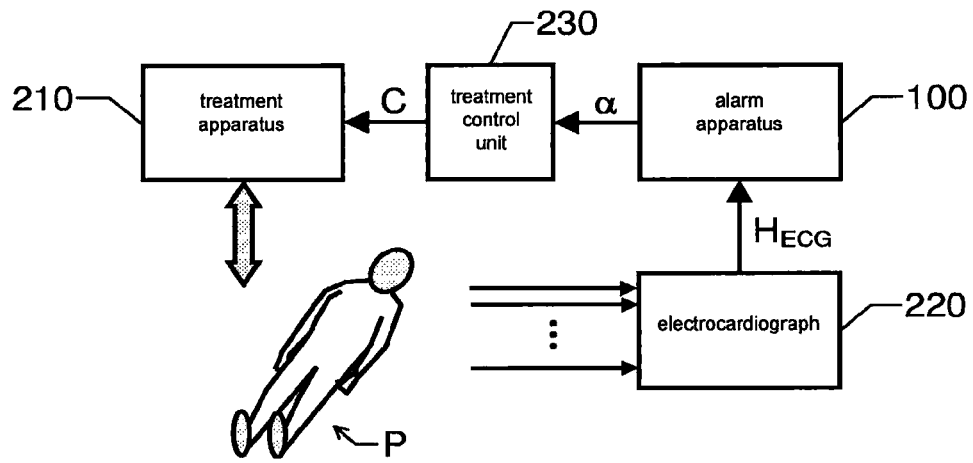
FIG. 2 shows an overview of a proposed medical system.

FIG. 2 shows an overview of a medical system according to one embodiment of the invention. The system includes a treatment apparatus 210 for performing an extracorporeal blood treatment of a patient P. Additionally, an electrocardiograph 220, a treatment control unit 230 and the proposed alarm apparatus 100 are included in the system. The electrocardiograph 220 registers an electrocardiogram signal $H_{ECG}$ of the patient P. For example, the electrocardiograph 220 may have a bandwidth of 0.05 Hz to 400 Hz, and the electrocardiogram signal $H_{ECG}$ may be a digitized signal which is sampled at a rate of 1000 Hz and has an amplitude resolution of 0.6 μV. Moreover, the electrocardiogram signal $H_{ECG}$ is preferably registered by means of a reduced set of electrodes, e.g. an EASI 5-lead system. The alarm apparatus 100 receives the electrocardiogram signal $H_{ECG}$. If either of the first or second alarm criteria is found to be fulfilled, the apparatus 100 produces an alarm signal α indicative of an estimated rapid blood pressure decrease. The treatment control unit 230 receives this signal α, and based thereon generates a control signal C to the treatment apparatus 210. The control signal C, in turn, causes the apparatus 210 to adjust at least one treatment parameter, e.g. the ultrafiltration rate, so that the estimated risk that the patient P enters a hypotension state is reduced.

According to one preferred embodiment of the invention, the control signal C effects a complete interruption of the treatment performed by the extracorporeal blood treatment apparatus 210.

Of course, the treatment control unit 230 need not be a separate unit (as illustrated in FIG. 2). Instead, this unit may be included in either one of the alarm apparatus 100, or the treatment apparatus 210.

Figure 3:
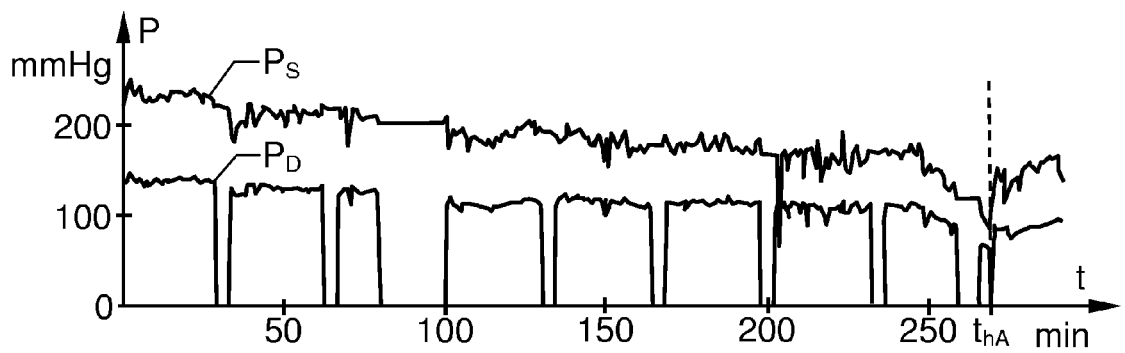
FIG. 3 shows a graph illustrating a first example of a patient's blood pressure variation during extracorporeal blood treatment.

FIG. 3 shows a graph, which illustrates how a patient's arterial blood pressure (sampled at 200 Hz) varied during an extracorporeal blood treatment when the invention was not applied. However, it is estimated that the above-proposed strategies would have been capable of predicting the blood pressure decrease at a point in time prior to $t_{hA}$ when the hypotension still could have been avoided had the appropriate measures been taken after generation of the alarm signal α.

The vertical axes show systolic pressures $P_S$ and diastolic pressures $P_D$, and the horizontal axes show the time t. In the example shown in FIG. 3 the patient suffered from acute symptomatic hypotension at a time $t_{hA}$=268 minutes after initiating the treatment. As can be seen in the graph, both pressures $P_S$ and $P_D$ drop rapidly before hypotension occurs.

Figure 4A:
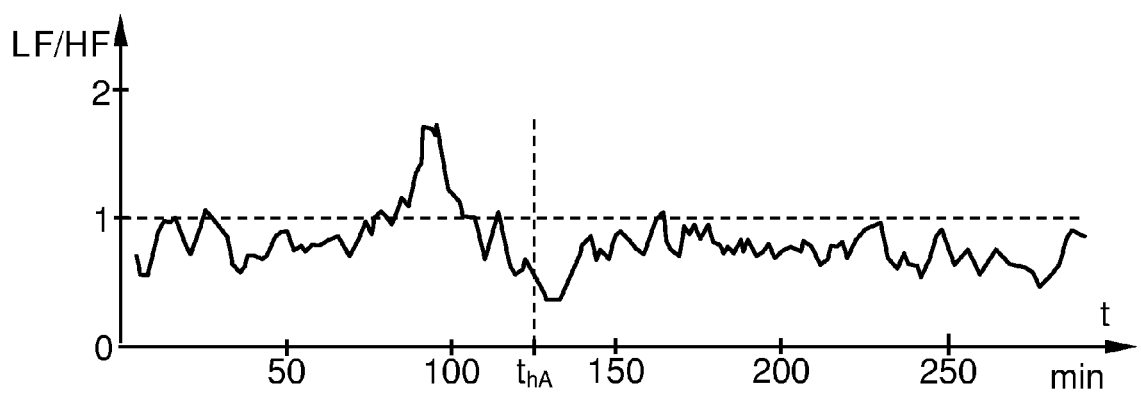
FIG. 4a shows a graph which illustrates how the ratio between an LF band and an HF band of a second patient's ECG power spectrum varies during an extracorporeal blood treatment.

FIG. 4a shows a graph which illustrates how a second patient'ratio LF/HF between a low-frequency (LF) band and a high-frequency (HF) band of an ECG power spectrum varies during an extracorporeal blood treatment. The HRV analysis was here performed according to the invention, i.e. all ectopic beats were handled before calculating the ratio LF/HF.

The vertical axis shows the ratio LF/HF and the horizontal axis represents the time t. A threshold value of LF/HF=1, indicated by means of a dashed line, illustrates the proposed first alarm criterion. As can be seen, in this example the ratio LF/HF is too low (i.e. below the threshold value 1) almost during the entire treatment. The patient made a slight head-up tilt around t≈100 minutes, which resulted in an increased ratio LF/HF exceeding the threshold value. Then, at t=$t_{hA}$ (≈125 minutes), the ratio LF/HF dropped sharply and acute symptomatic hypotension occurred.

Figure 4B:
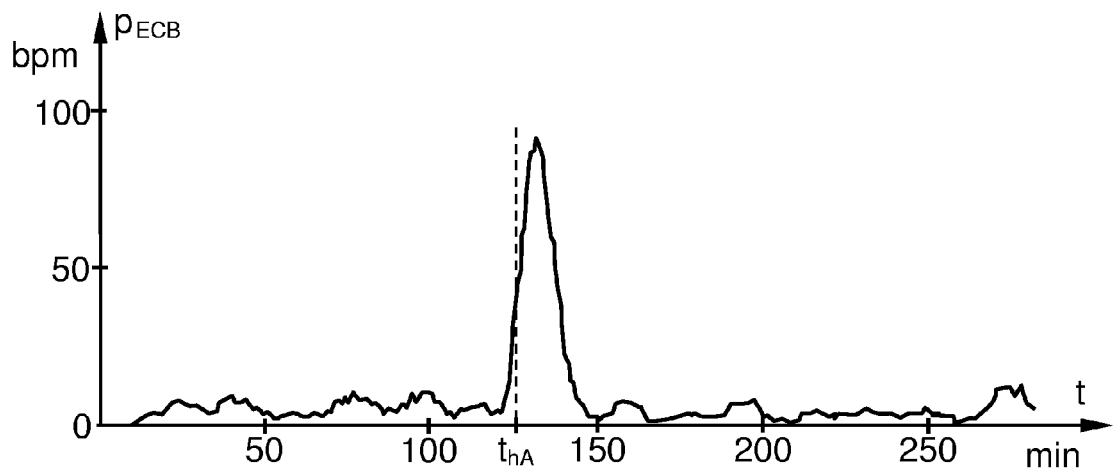
FIG. 4b shows a graph, corresponding to FIG. 4a, which demonstrates how the intensity of ectopic beats is developed for the second patient.

FIG. 4b shows a graph, corresponding to FIG. 4a, which demonstrates how the intensity of ectopic beats $p_{ECB}$ developed for the second patient. As is apparent from the graph, the intensity $p_{ECB}$ increased rapidly before t=$t_{hA}$. Thus, the proposed second alarm criterion would have been fulfilled before t=$t_{hA}$, and the hypotension could have been prevented.

Figure 5:
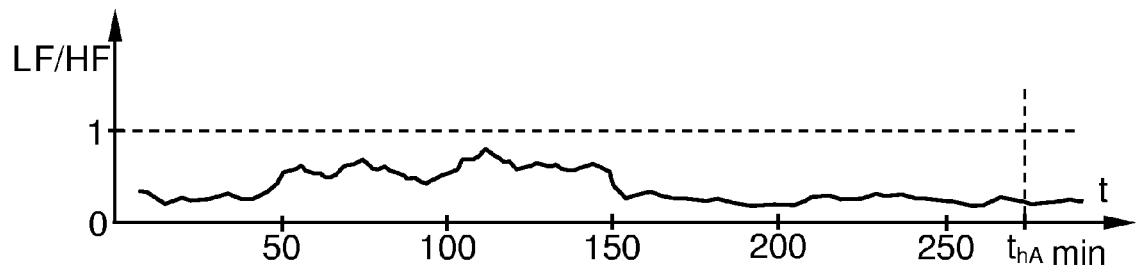
FIG. 5 shows a graph which illustrates how the ratio between an LF band and an HF band of a hypotension-prone patient's ECG power spectrum varies during an extracorporeal blood treatment.

FIG. 5 shows a graph which illustrates, by means of an example, how a ratio LF/HF between the LF band and the HF band of the ECG power spectrum may vary during an extracorporeal blood treatment for a patient who is relatively hypotension-prone. Here, there are no dramatic changes in the ratio LF/HF; only a minor increase between t=100 minutes to t=150 minutes due to eating. However, the ratio LF/HF never exceeds the threshold value 1, which indicates a high hypotension risk. Consequently, in this case, symptomatic hypotension occurred at t=$t_{hA}$ ($\approx$270 minutes).

Figure 6:
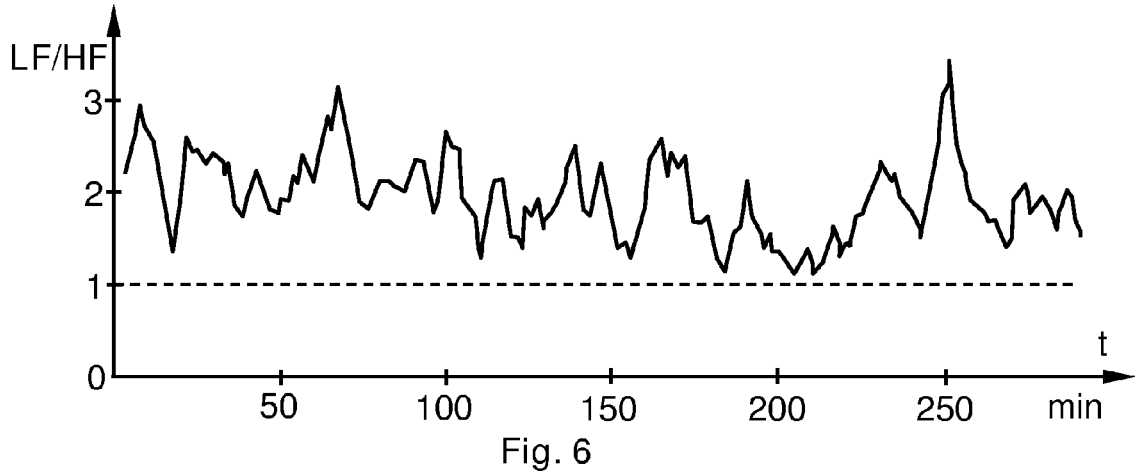
FIG. 6 shows a graph which illustrates how the ratio between an LF band and an HF band of a hypotension-resistant patient's ECG power spectrum varies during an extracorporeal blood treatment.

FIG. 6 shows a graph which illustrates, by means of an example, how the ratio LF/HF may vary during an extracorporeal blood treatment for a patient who is relatively hypotension-resistant. Again, the threshold value at LF/HF=1 is indicated by means of a dashed line. As opposed to the example shown in FIG. 5, the ratio LF/HF is here very high (permanently above 1, thus indicating a low hypotension risk), and although the ratio LF/HF varied substantially no hypotension occurred. This can be explained the patient being relatively hypotension-resistant and having a stable blood pressure.

Figure 7:
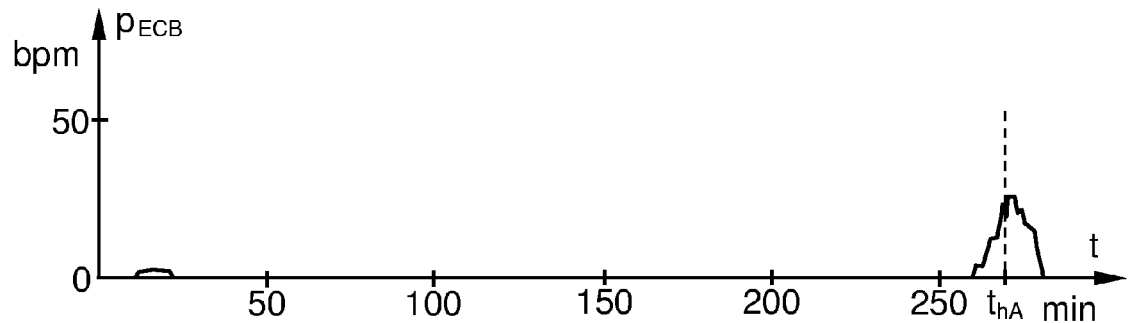
FIG. 7 shows a graph, which illustrates how the intensity of ectopic beats may be used as a basis for triggering an alarm signal.

FIG. 7 shows a graph, which illustrates how the intensity of ectopic beats $p_{ECB}$ developed for the above-mentioned first patient (see FIG. 3). In this case, practically no ectopic beats at all were registered until around t=260 minutes when the intensity of ectopic beats $p_{ECB}$ increased dramatically. Shortly there after, at $t_{hA}$=268 minutes, the patient suffered from acute symptomatic hypotension. An appropriately selected second alarm criterion according to the invention would certainly have predicted this.

Figure 8:
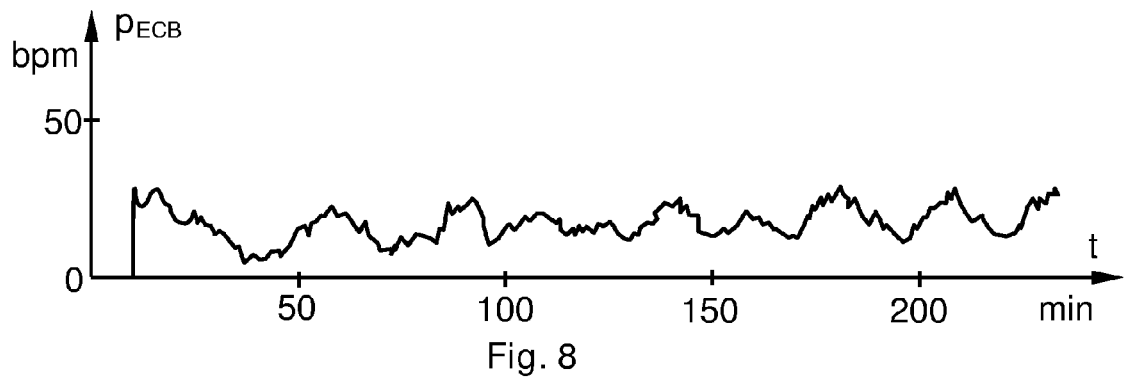
FIG. 8 shows a graph, which demonstrates that preferably a relative threshold value be used for triggering the alarm signal based on the intensity of ectopic beats, FIG. 9 demonstrates two proposed heart-rate-turbulence related parameters in a graph illustrating how the RR-intervals may vary in connection with an ectopic beat, FIGS. 10a, b show graphs which illustrate typical variations in the RR-intervals in connection with an ectopic beat for a hypotension-resistant and a hypotension-prone patient respectively, FIGS. 11a, b show diagrams illustrating the geometric properties of typical Poincaré plots of the RR-intervals for a hypotension-resistant and a hypotension-prone patient respectively.

FIG. 8 shows a graph over a patient's intensity of ectopic beats $p_{ECB}$ that is comparatively high throughout an entire extracorporeal blood treatment of the patient. However, here hypotension never occurred. This can be explained by the fact that the patient in this case is relatively hypotension-resistant. It should also be noted that the intensity of ectopic beats $p_{ECB}$ here never deviates exceedingly from a mean value (around approximately 30 bpm). Therefore, an appropriately selected second alarm criterion equivalent to roughly four times the mean intensity of ectopic beats, say at 120 bpm, would not have been fulfilled.

Returning now to the FIG. 1, we will now describe the heart-rate-turbulence analysis unit 150 in further detail.

The unit 150 is adapted to determine at least one heart-rate-turbulence (HRT) parameter $p_{HRT}$ based on the enhanced electrocardiogram signal $ECG_{CL}$. As mentioned earlier, the alarm generating unit 158 is adapted to trigger the alarm signal $\alpha$ if the at least one HRT parameter $p_{HRT}$ fulfils at least one third alarm criterion.

The rationale behind the test of the at least one HRT parameter $p_{HRT}$ is that, for normal subjects (i.e. being relatively hypotension resistant), the heart rate should increase immediately after a VEB, and then during a subsequent period return to baseline again. These short-term fluctuations in the heart rate are referred to as heart rate turbulence. It is believed that the heart rate is increased in order to compensate for a sudden local blood pressure drop induced by the VEB. Once the blood pressure level is restored, the heart rate returns to baseline again in order to stabilize the blood pressure. Consequently, HRT is desirable, and the degree of turbulence may be regarded as a subject's ability to recover from a local blood pressure drop, thereby avoiding hypotension.

We will now illustrate how the degree of turbulence can be measured with reference to FIG. 9. Here, a graph is shown, which illustrates how the RR-intervals may vary in connection with an ectopic beat for a patient. The horizontal axis shows the heart beat numbers #, and the vertical axis reflects the time between two consecutive R waves in the electrocardiogram, i.e. the RR-intervals $t_{RR}$.

The baseline is illustrated by means of a dashed line at an RR-interval around 700 ms. In this example, a first and a second beat are normal beats. However, for a third ectopic beat the RR-interval falls to approximately 500 ms, and for a fourth beat (i.e. between the ectopic beat and next normal beat) the RR-interval is prolonged to approximately 900 ms. Hence, these variations in the RR-intervals are induced by a VEB.

A first proposed HRT parameter $p_{HRT}$ expresses a turbulence-onset measure TO reflecting a relative change in the RR-intervals of the electrocardiogram signal $H_{ECG}$. TO is a measurement of the initial acceleration in the heart rate after the VEB. According to one preferred embodiment of the invention, the turbulence-onset measure TO is determined as a difference between an average RR-interval shortly after a particular VEB and an average RR-interval shortly before this beat divided by the average RR-interval shortly before said beat. This may be expressed as:

$$TO = 100 \cdot \frac{(RR_1 + RR_2) - (RR_{-2} + RR_{-1})}{(RR_{-2} + RR_{-1})} \ [\%]$$

where $RR_{-1}$ denotes the RR-interval immediately before the VEB, $RR_{-2}$ denotes the RR-interval before $RR_{-1}$, $RR_1$ denotes the RR-interval immediately after the VEB, and $RR_2$ denotes the RR-interval after $RR_1$.

In the example shown in the FIG. 9, TO$\approx$−7%, which is a healthy value. Essentially, any value below 0% can be regarded as healthy. Therefore, according to one preferred embodiment of the invention, the alarm generating unit 158 applies a first turbulence threshold value representing a zero alteration of the RR-interval between shortly before to shortly after a VEB, such that the alarm signal $\alpha$ is trigged if TO>zero.

A second parameter TS expresses a turbulence-slope measure reflecting how quickly the RR-intervals rise after a VEB, i.e. the declaration of the heart rate back to baseline again.

According to one preferred embodiment of the invention, the second parameter TS is determined based on a steepest (positive) slope of the RR-interval graph found over a first set of RR-intervals within a second set of RR-intervals following immediately after the VEB.

Healthy subjects generally have a heart rate declaration of at least 1 ms/RR-interval after the initial rate increase. Therefore, according to one preferred embodiment of the invention, after each VEB, a steepest positive slope over five RR-intervals (i.e. the above-mentioned first set) is determined within 15 RR-intervals (i.e. the second set above) following immediately after the VEB. Then the alarm generating unit 158 compares this steepest slope with a second turbulence threshold value representing one millisecond per RR-interval. If the second parameter TS is lower than this value, the alarm generating unit 158 triggers the alarm signal $\alpha$. However, also an exceedingly high TS value may indicate an unhealthy condition. Therefore, in the general case, the alarm generating unit 158 preferably triggers the alarm signal a if the second parameter TS falls outside a predefined interval delimited by a lower second threshold value and an upper second threshold value.

Naturally, according to the invention, the first and second sets may comprise any number of RR-intervals other than five and fifteen provided that second set>first set.

FIG. 10a shows a graph, which again illustrates how the RR-intervals may vary in connection with a VEB for a hypotension-resistant patient. The baseline here lies at an RR-interval around 600 ms. Then, comes a third beat, which is ectopic, wherein the RR-interval first decreases to 445 ms. The RR-interval to a following normal beat is prolonged to 800 ms. Subsequently, a short acceleration of the heart rate follows, and finally, the rate decelerates down to an RR-interval of 600 ms again.

FIG. 10b shows a graph illustrating an example of the variations in the RR-intervals in connection with VEB for a hypotension-prone patient. In this case, the subject has an RR-interval baseline at approximately 800 ms. This rate is temporarily altered around a third and a fourth heart beat, where the RR-intervals are 550 ms and 1050 ms respectively, due to the VEB. However, already at a fifth heartbeat the rate is back at the baseline 800 ms again. In other words, the steepest slope measured by the second parameter TS is inadequate, and due to the lack of compensation for the sudden blood pressure decrease after the VEB, the subject may experience nausea, and risks to faint. Of course, this risk is further increased if more VEB:s follow shortly, i.e. if the intensity of ectopic beats is relatively high. This parameter, in turn, is reflected by the second test signal $p_{EBC}$ generated by the ectopic-beat count unit 140.

Additional HRT parameters can be expressed in relation to a so-called Poincaré plot. This plot forms the basis for a well-known geometrical and non-linear time-domain analysis to assess the dynamics of the HRV. The Poincaré plot is a representation of a time series into a Cartesian plane, where each RR-interval is plotted as a function of a previous RR-interval. The most straightforward way to analyze the HRV dynamics is simply to visually inspect the shape and geometry of the plot. A quantitative analysis may be obtained by converting the two-dimensional plot into various one-dimensional views, for instance by fitting an ellipse to the plot shape. If this technique is applied, three popular indices may be defined, namely the standard deviation, SD, of the instantaneous beat-to-beat RR-interval variability (reflected by a minor axis $SD_1$ of the ellipse), the long term RR-interval variability (reflected by the major axis $SD_2$ of the ellipse) and the ratio there between (i.e. the axes ratio $SD_1/SD_2$).

According to one embodiment of the invention, the Poincaré plot is instead used to analyze the HRT. The inventors have found that, at least in patients with isolated VEB:s, a high degree of HRT is associated with a relatively large $SD_1$-value and a relatively large $SD_2$-value. Other measures, e.g. indicated by the above-mentioned first and second parameters TO and TS, have revealed that HRT appeared to be present in patients being comparatively resistant to hypotension when such high $SD_1$- and $SD_2$-values were registered.

Figure 11A:
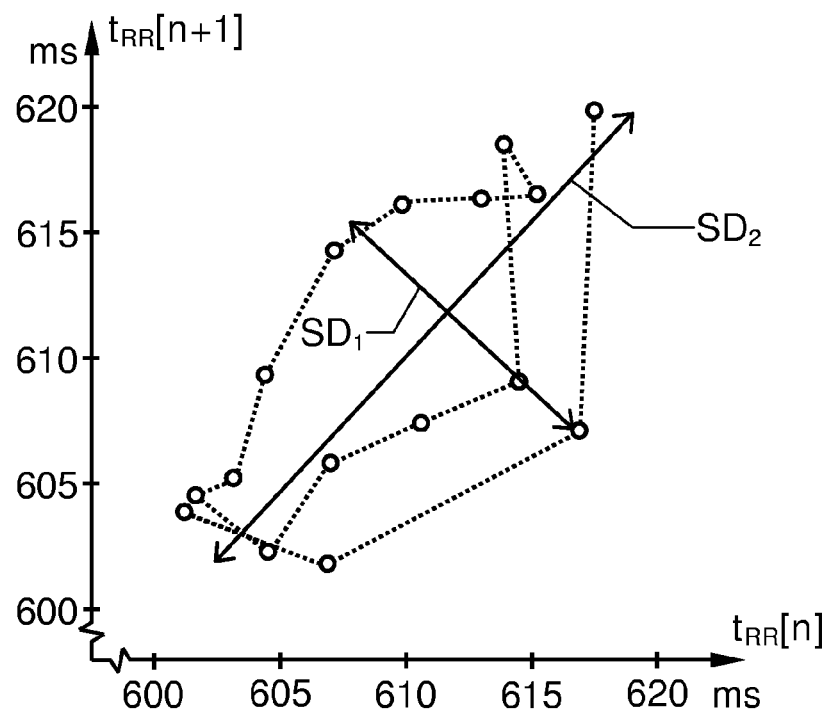

FIG. 11a shows a Poincaré plot over a number of the RR-intervals for a hypotension-resistant patient. In the diagram, every second RR-interval is represented along the horizontal axis $t_{RR}[n]$ and every second is represented along the vertical axis $t_{RR}[n+1]$ in a cyclic manner. Here, the variation in the RR-intervals is relatively large, so the geometrical proportions of the plot become rather large (which is equivalent to relatively high $SD_1$- and $SD_2$-values).

Figure 11B:
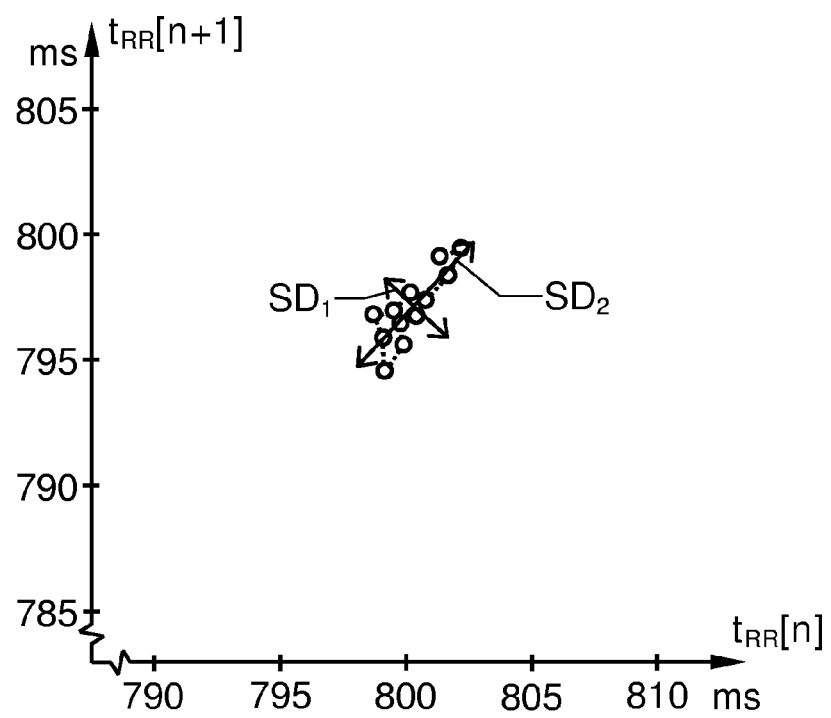

However, in patients being relatively prone to hypotension, comparatively low $SD_1$- and $SD_2$-values are typically registered indicating that an insufficient HRT is present. FIG. 11b shows a Poincaré plot over a number of the RR-intervals for a hypotension-prone patient. As can be seen, the geometrical proportions of the plot are here rather small (which is equivalent to relatively low $SD_1$- and $SD_2$-values).

Due to the above-described differences in the geometrical proportions of the Poincaré plot, these plots are proposed as one analysis basis for HRT.

According to one preferred embodiment of the invention the standard deviation values $SD_1$ and $SD_2$ are used as a pair of quantities expressing the geometric properties of a Poincaré plot in respect of the RR-intervals of the registered electrocardiogram signal $H_{ECG}$. Then, the at least one third alarm criterion is regarded as fulfilled if the pair of third quantities $SD_1$ and $SD_2$ are estimated to represents an RR-interval variation below a third threshold value.

Specifically, the RR-interval variation may be deemed to be below the third threshold value if a product between a first quantity (given by the minor axis $SD_1$-value) and a second quantity (given by the major axis $SD_2$-value) falls below a threshold area estimate. Alternatively, or as a complement thereto, the third threshold value may be considered not reached if at least one of the first and second quantities $SD_1$ and $SD_2$ falls below a predetermined limit value, and/or a ratio $SD_1/SD_2$ (or $SD_2/SD_1$) between the first quantity $SD_1$ and the second quantity $SD_2$ falls outside a predetermined interval (i.e. is too high or too low).

Figure 12:
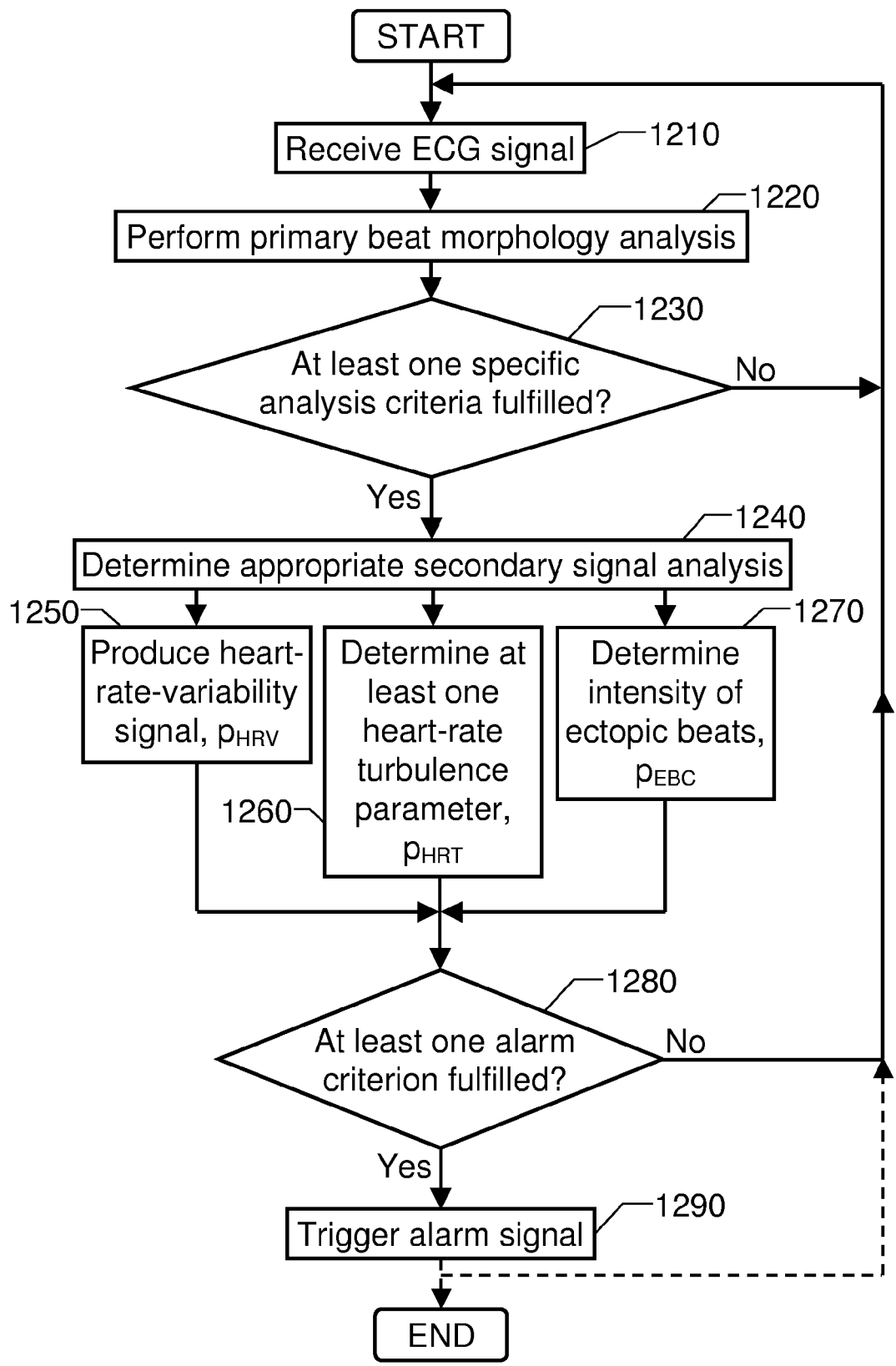
FIG. 12 shows a flow diagram which illustrates the general method according to the invention.

In order to sum up, the general method according to the invention will be described below with reference to the flow diagram in FIG. 12.

A first step 1210 receives an electrocardiogram signal of a patient, for instance the above-described basic electrocardiogram signal $H_{ECG}$. Then, a step 1220 performs a primary beat morphology analysis, wherein heartbeats are discriminated in the electrocardiogram signal and each beat is classified into one out of at least two different beat categories. The step 1220 also associates each signal segment of the electrocardiogram signal with relevant event-type data, i.e. information that reflects a beat category represented by the signal during that segment. According to the invention, the event-type data and the basic electrocardiogram signal together forming an enhanced electrocardiogram signal.

A step 1230 determines whether at least one specific analysis criterion is fulfilled, i.e. if one or more secondary signal analyses should be performed in respect of the electrocardiogram signal. If it is found that no such criterion is met, the procedure loops back to the step 1210. Otherwise a step 1240 follows.

The step 1240 performs any types of secondary analyses determined by the step 1230 based on the enhanced electrocardiogram signal. This means that up to at least two different types of secondary analyses may be carried out, and a respective resulting test signal be produced.

According to preferred embodiments of the invention the secondary analyses include a HRV analysis through which a first test signal $p_{HRV}$ is produced, an EBC analysis through which a second test signal $p_{HRT}$ is produced and a HRT analysis through which a third test signal $p_{HRT}$ is produced. Steps 1250, 1270 and 1260 represent these analyses respectively.

Thereafter, a step 1280 investigates whether any of the test signals $p_{HRV}$, $p_{EBC}$, or $p_{HRT}$ fulfills at least one alarm criterion. If so, a step 1290 follows, and otherwise the procedure loops back to the step 1210. The step 1290 triggers an alarm signal indicative of an estimated rapid blood pressure decrease. After that, the procedure may either end, or loop back to the step 1210 for a continued surveillance of the hypotension risk.

It is worth noting that the sequential procedure described above is only relevant for a particular segment of the electrocardiogram signal. Thus, in an implementation, e.g. a second signal segment is received according the step 1210 while a primary beat morphology analysis is performed in respect of a first signal segment according to the step 1220, and so on.

Furthermore, all of the process steps, as well as any subsequence of steps, described with reference to the FIG. 12 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code; object code, a code intermediate source and object code such as in partially compiled form, or in any other form suitable for use in the implementation of the process according to the invention. The carrier may be any entity or device capable of carrying the program. For example, the carrier may comprise a storage medium, such as a Flash memory, a ROM (Read Only Memory), for example a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

It should be noted that in this specification the term "predict" is given a very broad meaning, so that the point in time when a fulfilled alarm criterion is established and the point in time when said blood pressure decrease actually occurs may essentially coincide. Consequently, the alarm signal in this case represents a detection of the rapid blood pressure decrease rather than a prediction thereof.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. An alarm apparatus for predicting a rapid blood pressure decrease in a patient undergoing extracorporeal blood treatment, the apparatus comprising:
   an input interface configured to receive a basic electrocardiogram signal of the patient;
   a primary beat morphology analysis unit configured to:
      discriminate heartbeats in the basic electrocardiogram signal, said basic electrocardiogram signal having a plurality of signal segments,
      classify each discriminated heartbeat into one out of at least two different beat categories of which one beat category represents a beat whose morphology is typical for the patient,
      associate each of the plurality of signal segments of the basic electrocardiogram signal with event-type data reflecting one of said at least two different beat categories represented by the signal during that segment, the event-type data and the basic electrocardiogram signal together forming an enhanced electrocardiogram signal, and
      determine a number of secondary signal analyses to be performed in respect of the basic electrocardiogram signal;
   a bank of secondary analysis units configured to:
      receive and use the enhanced electrocardiogram signal to perform up to at least two different types of said secondary analyses in response to control instructions from the primary beat morphology analysis unit, and for each analysis performed, produce a respective test signal,
      wherein the bank of secondary analysis units comprises at least two different secondary analysis units selected from a group of:
         a heart-rate-variability analysis unit configured to produce a first test signal describing a ratio between a low-frequency band and a high-frequency band of a power spectrum representation of the basic electrocardiogram signal,
         an ectopic-beat count unit configured to produce a second test signal describing an intensity of ectopic beats, and
         a heart-rate-turbulence analysis unit configured to produce at least one third test signal describing at least one heart-rate-turbulence parameter; and
   an alarm generating unit configured to:
      receive the test signals,
      investigate whether any of the test signals fulfill at least one alarm criterion, and if so,
      trigger an alarm signal indicative of an estimated rapid blood pressure decrease, wherein the alarm generating unit is configured to trigger the alarm signal:
         if the first test signal fulfills a first alarm criterion, or
         if the second test signal fulfills a second alarm criterion, or
         if the at least one third test signal fulfills at least one third alarm criterion, wherein the at least one third test signal comprises at least one of:
            a first parameter expressing a turbulence-onset measure reflecting a relative change in RR-intervals of the basic electrocardiogram signal during a period following a particular ectopic beat,
            a second parameter expressing a turbulence-slope measure reflecting a rise rate of the RR-intervals during a period following a particular ectopic beat, and
            a pair of third quantities expressing geometric properties of a Poincaré plot in respect of the RR-intervals of the basic electrocardiogram signal during a period following a particular ectopic beat, wherein the at least one third alarm criterion is fulfilled if:
               the first parameter exceeds a first turbulence threshold value,
               the second parameter is outside an interval delimited by a lower second turbulence value and an upper second turbulence value, or
               the pair of third quantities is estimated to represent an RR-interval variation below a third threshold value, wherein the RR-interval variation is estimated to be below the third threshold value if, in the pair of third quantities:
                  a product between a first quantity and a second quantity falls below a threshold area estimate, at least one of the first and second quantities falls below a predetermined limit value, or
a ratio between the first quantity and the second quantity falls outside a predetermined interval.

2. An alarm apparatus according to claim 1, wherein the first alarm criterion is fulfilled if the first test signal is below a first threshold value, and the second alarm criterion is fulfilled if the second test signal exceeds a second threshold value.

3. An alarm apparatus according to claim 2, wherein the second threshold value represents a number equivalent to approximately four times a mean intensity of ectopic beats.

4. An alarm apparatus according to claim 1, wherein
the first parameter is determined as a difference between an average RR-interval shortly after a particular ventricular ectopic beat and an average RR-interval shortly before this beat divided by the average RR-interval shortly before said beat,
and the first turbulence threshold value represents a zero alteration of the RR-interval between shortly before to shortly after said ventricular ectopic beat.

5. An alarm apparatus according to claim 1, wherein
the second parameter is determined based on a steepest slope found over a first set of RR-intervals within a second set of RR-intervals following immediately after said ventricular ectopic beat in a function expressing a time difference between consecutive R waves in the basic electrocardiogram signal, and
the lower second turbulence value represents one millisecond per RR-interval.

6. An alarm apparatus according to claim 1, wherein the heart-rate-variability analysis unit comprises a spectral analysis module configured to produce the first test signal by:
transforming a heart rate signal based on the enhanced electrocardiogram signal into a power spectrum representation of the basic electrocardiogram signal, and
calculating the ratio between the low-frequency band and the high-frequency band of said power spectrum representation.

7. An alarm apparatus according to claim 6, wherein the low-frequency band ranges from approximately 0.04 Hertz to approximately 0.15 Hertz, the high-frequency band ranges from approximately 0.15 Hertz to approximately 0.40 Hertz, and the first threshold value is approximately equal to one.

8. An alarm apparatus according to claim 6, wherein the heart-rate-variability analysis unit comprises a rate detector module configured to receive and use the enhanced electrocardiogram signal to produce the heart rate signal.

9. An alarm apparatus according to claim 1, wherein said event-type data comprises a normal beat representing a beat whose morphology is typical for the patient, and at least one of the beat categories from a group including:
a ventricular ectopic beat representing a beat whose morphology differs substantially from a normal sinus beat,
a supraventricular ectopic beat representing a beat whose morphology differs from a normal sinus beat with respect to a P-wave morphology, and
a prolonged RR-interval representing a morphology wherein a time distance between two consecutive beats exceeds a typical time distance between two such beats for the patient by a predetermined proportion.

10. An alarm apparatus according to claim 9, wherein said event-type data further comprises at least one of:
an artifact representing a beat which fulfills none of the criteria for a normal beat, a ventricular ectopic beat, a supraventricular ectopic beat, and a prolonged RR-interval, and
noise representing undesired energy of the basic electrocardiogram signal.

11. A medical system comprising an apparatus configured to perform an extracorporeal blood treatment of a patient, wherein the system comprises:
an electrocardiograph configured to register a basic electrocardiogram signal of the patient,
an alarm apparatus according to claim 1 receiving said basic electrocardiogram signal, and
a treatment control unit configured to receive the alarm signal from the alarm apparatus, and based on the alarm signal, transmit a control signal, wherein the control signal is configured to cause an adjustment of at least one treatment parameter in the extracorporeal blood treatment apparatus such that an estimated risk that the patient enters a hypotension state is reduced.

12. A medical system according to claim 11, characterized in that the control signal is configured to effect an interruption of the treatment performed by the extracorporeal blood apparatus.

13. A method for predicting a rapid blood pressure decrease in a patient undergoing extracorporeal blood treatment, involving:
receiving a basic electrocardiogram signal of the patient, and
producing at least one processed signal on the basis of the basic electrocardiogram signal, said basic electrocardiogram signal having a plurality of signal segments, characterized by:
discriminating heart beats in the basic electrocardiogram signal,
classifying each discriminated heart beat into one out of at least two different beat categories of which one beat category represents a beat whose morphology is typical for the patient,
associating each of the plurality of signal segments of the basic electrocardiogram signal with event-type data reflecting one of said at least two different beat categories represented by the signal during a particular signal segment, the event-type data and the basic electrocardiogram signal together forming an enhanced electrocardiogram signal,
determining a number of secondary signal analyses to be performed in respect of the basic electrocardiogram signal, the secondary signal analyses comprising at least two different secondary analyses selected from a group including:
a heart-rate-variability analysis producing a first test signal describing a ratio between a low-frequency band and a high-frequency band of a power spectrum representation of the basic electrocardiogram signal,
an ectopic-beat analysis producing a second test signal describing an intensity of ectopic beats, and
a heart-rate-turbulence analysis producing at least one third test signal describing at least one heart-rate-turbulence parameter,
performing, based on the enhanced electrocardiogram signal, up to at least two different types of said secondary analyses to produce a respective resulting test signal, and
investigating whether any of the test signals fulfill at least one alarm criterion, and if so,
triggering an alarm signal indicative of an estimated rapid blood pressure decrease, wherein the alarm signal is triggered:
if the first test signal fulfills a first alarm criterion, if the second test signal fulfils a second alarm criterion, or if the at least one third test signal fulfils at least one third alarm criterion, wherein the at least one third test signal comprises at least one of:

a first parameter expressing a turbulence-onset measure reflecting a relative change in the RR-intervals of the basic electrocardiogram signal during a period following a particular ectopic beat, a second parameter expressing a turbulence-slope measure reflecting a rise rate of the RR-intervals during a period following a particular ectopic beat, and a pair of third quantities expressing geometric properties of a Poincaré plot in respect of the RR-intervals of the basic electrocardiogram signal during a period following a particular ectopic beat, wherein the at least one third alarm criterion being fulfilled if:

the first parameter exceeds a first turbulence threshold value, the second parameter is outside an interval delimited by a lower second turbulence value and an upper second turbulence value, or the pair of third quantities is estimated to represent an RR-interval variation below a third threshold value, wherein the RR-interval variation is estimated to be below the third threshold value if, in the pair of third quantities:

a product between a first quantity and a second quantity falls below a threshold area estimate, at least one of the first and second quantities falls below a predetermined limit value, or a ratio between the first quantity and the second quantity falls outside a predetermined interval.

14. A method according to claim 13, wherein the first alarm criterion is fulfilled if the first test signal is below a first threshold value, and the second alarm criterion is fulfilled if the second test signal exceeds a second threshold value.

15. A method according to claim 14, wherein the second threshold value represents a number equivalent to approximately four times a mean intensity of ectopic beats.

16. A method according to claim 13, further comprising determining the first parameter as a difference between an average RR-interval shortly after a particular ventricular ectopic beat and an average RR-interval shortly before this beat divided by the average RR-interval shortly before said beat, and the first turbulence threshold value represents a zero alteration of the RR-interval between shortly before to shortly after said ventricular ectopic beat.

17. A method according to claim 13, further comprising:

determining the second parameter based on a steepest slope found over a first set of RR-intervals within a second set of RR-intervals following immediately after said ventricular ectopic beat in a function expressing a time difference between consecutive R waves in the basic electrocardiogram signal, and the lower second turbulence value represents one millisecond per RR-interval.

18. A method according to claim 13, wherein the heart-rate-variability analysis comprises a spectral analysis wherein the first test signal is produced by:

transforming a heart rate signal based on the enhanced electrocardiogram signal into a power spectrum representation of the basic electrocardiogram signal, and calculating the ratio between the low-frequency band and the high-frequency band of said power spectrum representation.

19. A method according to claim 13, wherein the low-frequency band ranges from approximately 0.04 Hertz to approximately 0.15 Hertz, the high-frequency band ranges from approximately 0.15 Hertz to approximately 0.40 Hertz, and the first threshold value is approximately equal to one.

20. A method according to claim 13, wherein said event-type data comprises a normal beat representing a beat whose morphology is typical for the patient, and at least one of the beat categories from a group including:

a ventricular ectopic beat representing a beat whose morphology differs substantially from a normal sinus beat, a supraventricular ectopic beat representing a beat whose morphology differs from a normal sinus beat with respect to a P-wave morphology, and a prolonged RR-interval representing a morphology wherein a time distance between two consecutive beats exceeds a typical time distance between two such beats for the patient by a predetermined proportion.

21. A method according to claim 20, wherein said event-type data further comprises at least one of:

an artifact representing a beat which fulfills none of the criteria for a normal beat, a ventricular ectopic beat, a supraventricular ectopic beat, and a prolonged RR-interval, and noise representing undesired energy of the basic electrocardiogram signal.

22. A non-transitory computer readable medium having a program recorded thereon, the program being configured to make a computer control the steps of claim 13.

* * * * *